(12) United States Patent
Liang et al.

(10) Patent No.: US 8,962,275 B2
(45) Date of Patent: Feb. 24, 2015

(54) ANTI-α5β1 ANTIBODIES AND USES THEREOF

(75) Inventors: Wei-Ching Liang, Foster City, CA (US); Gregory D. Plowman, New York, NY (US); Yan Wu, Foster City, CA (US); Weilan Ye, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 321 days.

(21) Appl. No.: 13/335,632

(22) Filed: Dec. 22, 2011

(65) Prior Publication Data

US 2013/0095096 A1 Apr. 18, 2013

Related U.S. Application Data

(63) Continuation of application No. 12/729,999, filed on Mar. 23, 2010, now Pat. No. 8,124,740.

(60) Provisional application No. 61/163,241, filed on Mar. 25, 2009.

(51) Int. Cl.
| | | |
|---|---|---|
| C07H 21/04 | (2006.01) | |
| C12P 21/06 | (2006.01) | |
| C12N 15/87 | (2006.01) | |
| C12N 1/20 | (2006.01) | |
| C12N 15/74 | (2006.01) | |
| C07K 16/28 | (2006.01) | |
| C07K 16/22 | (2006.01) | |
| A61K 39/00 | (2006.01) | |

(52) U.S. Cl.
CPC ............ *C07K 16/2842* (2013.01); *C07K 16/22* (2013.01); *A61K 2039/505* (2013.01); *A61K 2039/507* (2013.01); *C07K 2317/24* (2013.01); *C07K 2317/56* (2013.01); *C07K 2317/565* (2013.01); *C07K 2317/92* (2013.01)
USPC ..... 435/69.1; 435/455; 435/252.3; 435/320.1; 536/23.53

(58) Field of Classification Search
None
See application file for complete search history.

(56) References Cited

U.S. PATENT DOCUMENTS

| | | | |
|---|---|---|---|
| 5,540,933 A | 7/1996 | Ruoslahti et al. | |
| 5,583,203 A | 12/1996 | Hemler et al. | |
| 5,627,263 A | 5/1997 | Ruoslahti et al. | |
| 5,766,857 A | 6/1998 | Ruoslahti et al. | |
| 5,981,478 A | 11/1999 | Ruoslahti et al. | |
| 5,985,278 A | 11/1999 | Mitijans et al. | |
| 6,242,577 B1 | 6/2001 | Ruoslahti et al. | |
| 6,852,318 B1 | 2/2005 | Varner | |
| 7,056,506 B2 | 6/2006 | Varner | |
| 7,067,619 B2 | 6/2006 | Ruslahti et al. | |
| 7,189,507 B2 | 3/2007 | Mack et al. | |
| 7,276,589 B2 | 10/2007 | Ramakrishnan | |
| 7,285,268 B2 | 10/2007 | Ramakrishnan et al. | |
| 7,311,911 B2 | 12/2007 | Varner | |
| 7,435,589 B2 | 10/2008 | Mack et al. | |
| 7,662,384 B2 | 2/2010 | Ramakrishnan et al. | |
| 8,124,740 B2 * | 2/2012 | Liang et al. ................. | 530/387.3 |
| 2002/0015970 A1 | 2/2002 | Murray et al. | |
| 2002/0019330 A1 | 2/2002 | Murray et al. | |
| 2003/0124579 A1 | 7/2003 | Mack et al. | |
| 2003/0152926 A1 | 8/2003 | Murray et al. | |
| 2003/0232350 A1 | 12/2003 | Afar et al. | |
| 2004/0009494 A1 | 1/2004 | Murray et al. | |
| 2004/0033495 A1 | 2/2004 | Murray et al. | |
| 2004/0076955 A1 | 4/2004 | Mack et al. | |
| 2004/0253606 A1 | 12/2004 | Aziz et al. | |
| 2004/0259152 A1 | 12/2004 | Murray et al. | |
| 2005/0002930 A1 | 1/2005 | Johnson et al. | |
| 2006/0008415 A1 | 1/2006 | Kaisheva et al. | |
| 2006/0127407 A1 | 6/2006 | Chen et al. | |
| 2006/0241067 A1 | 10/2006 | Varnet et al. | |
| 2007/0042360 A1 | 2/2007 | Afar et al. | |
| 2007/0059748 A1 | 3/2007 | Afar et al. | |
| 2007/0161016 A1 | 7/2007 | Afar et al. | |
| 2008/0026033 A1 | 1/2008 | Ramakrishnan | |
| 2008/0026458 A1 | 1/2008 | Ramakrishnan | |
| 2008/0113898 A1 | 5/2008 | Varner | |
| 2008/0188641 A1 | 8/2008 | Varner | |
| 2008/0233108 A1 | 9/2008 | Varner | |
| 2008/0260732 A1 | 10/2008 | Ramakrishnan | |
| 2009/0041785 A1 | 2/2009 | Johnson et al. | |
| 2009/0081207 A1 | 3/2009 | Menrad et al. | |
| 2009/0111828 A1 | 4/2009 | Kettle et al. | |
| 2009/0137601 A1 | 5/2009 | Barry et al. | |
| 2009/0220504 A1 | 9/2009 | Chuntharapa et al. | |

FOREIGN PATENT DOCUMENTS

| | | |
|---|---|---|
| EP | 1049718 | 11/2000 |
| EP | 1075277 | 2/2009 |
| JP | 2007-524605 A | 8/2007 |
| JP | 2007-530584 A | 11/2007 |

(Continued)

OTHER PUBLICATIONS

Akiyama et al., "Analysis of Fibronectin Receptor Function With Monoclonal Anitbodies: Roles in Cell Adhesion, Migration, Matrix Assembly, and Cytoskeletal Organization" The Journal of Cell Biology 109:863-875 (Aug. 1989).
Akiyama et al., "Fibronectin and Integrins in Invasion and Metastasis" Cancer Metastasis Review 14:173-189 ( 1995).
Baluk et al., "Cellular Abnormalities of Blood Vessels as targets in Cancer" Current Opinion in Genetics & Development 15:102-111 ( 2005).
Bauer et al., "The Functional Role of Integrins in Cell Adhesion, Motility and Differentiation (Integrins, Extracellular Matrix)" Dissertation Abstracts International 54/06-B:3009 ( 1993).
BDBiosciences (Oct.-Nov. 2004). "CD49e Purified Mouse Anti-Human Monoclonal Antibody' BD Pharmingen Technical Data Sheet," (Oct.-Nov. 2004) http://www.bdbiosciences.com.

(Continued)

*Primary Examiner* — Maher Haddad
(74) *Attorney, Agent, or Firm* — Morrison & Foerster LLP

(57) ABSTRACT

The present invention provides new anti-α5β1 antibodies, compositions and kits comprising the antibodies, and methods of making and using the antibodies.

9 Claims, 12 Drawing Sheets

(56) References Cited

FOREIGN PATENT DOCUMENTS

| JP | 2011-526480 A | 10/2011 |
|---|---|---|
| WO | 95/14714 | 6/1995 |
| WO | 99/58139 | 11/1999 |
| WO | 00/64480 | 11/2000 |
| WO | 01/11086 | 2/2001 |
| WO | 02/079492 | 10/2002 |
| WO | 02/086443 | 10/2002 |
| WO | 02/098358 | 12/2002 |
| WO | 02/102235 | 12/2002 |
| WO | 03/003906 | 1/2003 |
| WO | 03/025138 | 3/2003 |
| WO | 03/042661 | 5/2003 |
| WO | 04/001384 | 12/2003 |
| WO | 2004/048938 | 6/2004 |
| WO | 2004/056308 | 7/2004 |
| WO | 2004/089988 | 10/2004 |
| WO | 2005/092073 | 10/2005 |
| WO | 2006/004736 | 1/2006 |
| WO | 2007/060408 | 5/2007 |
| WO | 2007/060409 | 5/2007 |
| WO | 2007/091046 | 11/2007 |
| WO | 2007/134876 | 11/2007 |
| WO | 2008/060645 | 5/2008 |
| WO | 2009/042746 | 4/2009 |
| WO | 2009/100110 | 8/2009 |
| WO | 2010/111254 | 9/2010 |

OTHER PUBLICATIONS

Bliss et al., "he Role of β1 Integrins in Adhesion of Two Breast Carcinoma Cell Lines to a Model Endothelium" Clinical & Experimental Metastasis 13(3):173-183 (Feb. 24, 1995).
Braden, et al., "Structural Features of the Reactions Between Antibodies and Protein Antigens" FASEB J. 9:9-16 ( 1995).
Burrows et al., "Fine Mapping of Inhibitory Anti-α5 Monoclonal Antibody Epitopes That Differentially Affect Integrin-Ligand Binding" Biochemical Journal 344:527-533 ( 1999).
Carter et al., "Potent Antibody Therapeutics by Design" Nature Review, Immunology 6:343-344 (2006).
Chi et al., "Broadly Neutralizing Anti-hepatitis B Virus Antibody Reveals a Complementarily Determining Region H3 Lid-Opening Mechanism" Proc. Natl. Acad. Sci. USA 104:9230-9235 ( 2007).
Chunmeng et al., "Effects of Dermal Multipotent Cell Transplantation on Skin Wound Healing" The Journal of Surgical Research 121(1):13-19 (Sep. 2004).
Cobleigh et al., "A Phase I/II Dose-Escalation Trial of Bevacizumab in Previously Treated Metastatic Breast Cancer" Semin. Oncol. 30( Suppl 16):117-124 ( 2003).
Collo et al., "Endothelial Cell Integrin α5β1 Expression is Modulated by Cytokines and During Migration in Vitro" Journal of Cell Science 112:569-578 (Jan. 25, 1999).
Danen et al., "Emergence of α5β1 Fibronectin- and αvβ3 Vitronectin-Receptor Expression in Melanocytic Tumour Progression" Histopathology 24:249-256 (Sep. 28, 1993).
Davies et al., "Affinity Improvement of Single Antibody VH Domains: Residues in all Three Hypervariable Regions Affect Antigen Binding" Immunotechnology 2(3):169-179 (1996).
Du Manoir et al., "Strategies for Delaying or Treating in Vivo Acquired Resistance to Trastuzumab in Human Breast Cancer Xenografts" Clinical Cancer Research, The American Association for Cancer Research 12(3):904-916 (Feb. 1, 2006).
Economopoulou et al., "nhibition of Pathologic Retinal Neovascularization by α-Defensins" Blood 106(12):3831 (Dec. 2005).
Eming et al., "Regulation of Angiogenesis: Wound Healing as a Model" Progress in Histochemistry and Cytochemistry 42:115-170 (Jun. 21, 2007).
Ferrara et al., "VEGF as a Therapeutic Target in Cancer" Oncology 69( Suppl 3):11-16 (Nov. 21, 2005).

Ferrara et al., "Angiogenesis as a Therapeutic Target," Nature 438(7070):967-974 (Dec. 15, 2005).
Fogerty et al., "Inhibition of Fibronectin to Matrix Assembly Sites by Anti-Integrin (α5β1) Antibodies" The Journal of Cell Biology 111:699-708 (Aug. 1990).
Gilcrease et al., "Integrin Signaling in Epithelial Cells" Cancer Letters 247:1-25 ( 2007).
Gong et al., "Role of α5β1 Integrin in Determining Malignant Properties of Colon Carcinoma Cells" Cell Growth & Differentiation 8:83-90 (Jan. 1997).
Hermanson Bioconjugate Techniques , Chapter 10, San Diego:Academic Press,: p. 456 (1996).
Holt et al., "Domain Antibodies: Proteins for Therapy" Trends in Biotechnology 21(11):484-490 (Nov. 2003).
Humphries et al., "Dual Functionality of the Anti-β1 Integrin Antibody, 12G10, Exemplifies Agonistic Signalling From the Ligand Binding Pocket of Integrin Adhesion Receptors" Journal of Biological Chem. 280(11):10234-10243 (Mar. 18, 2005).
Jin et al., "Integrins: Role in Cancer Development and as Treatment Targets" Br. J. Cancer 90(3):561-565 (Feb. 9, 2004).
Kim et al., "Regulation of Angiogenesis in Vivo by Ligation of Integrin α5β1 With the Central Cell-Binding Domain of Fibronectin" American Journal of Pathology 156(4):1345-1362 (Apr. 2000).
Kirsh et al., "Anti-Agniogenic Treatment Strategies for Malignant Brain Tumors" J. Neurooncology (Oct.-Nov.), 50(1-2):149-163 ( 2001).
Koivunen et al., "Isolation of a Highly Specfic Ligand for the α5β1 Integrin from a Phage Display Library" The Journal of Cell Biology 124(3):373-380 (Feb. 1994).
Kussie et al., "A Single Engineered Amino Acid Substitution Changes Antibody Fine Specificity" J. Immunology 152(1):146-152 ( 1994).
Liapis et al., "Expression of αvβ3 Integrin is Less Frequent in Ovarian Epithelial Tumors of Low Malignant Potential in Contrast to Ovarian Carcinomas" Human Pathology 28(4):443-449 (Apr. 1997).
Lyseng-Williamson et al., "Bevacizumab: A Review of Its Use in Advanced Colorectal Cancer, Breast Cancer, and NSCLC" American Journal of Cancer 5(1):43-60 ( 2006).
Magnussen et al., "Rapid Access of Antibodies to α5β1 Integrin Overexpressed on the Luminal Surface of Tumor Blood Vessels" Cancer Research 65(7):2712-2721 (Apr. 1, 2005).
Mettouchi et al., "Distinct Roles of β1 Integrins During Angiogenesis" European Journal of Cell Biology 85:243-247 ( 2006).
Mould et al., "Defining the Topology of Integrin α5β1-Fibronectin Interactions Using Inhibitory Anti-α5 and anti-β1 Monoclonal Antibodies. Evidence That the Synergy Sequence of Fibronectin is Recognized by the Amino-Terminal Repeats of the α5 Subunit" J. Biol. Chem. 272(28):17283-17292 (Jul. 11, 1997).
Mousa et al., "Anti-Integrins as a Potential Therapeutic Target in Angiogenesis" Expert Opinion on Therapeutic Patents 9(9):1237-1248 ( 1999).
Muether et al., "ntegrin Alpha5beta 1-Inhibiting Small Molecule Reduces Corneal Neovascularisation" (Database Biosis, Biosciences Information Services (Database Accession No. PREV200600052329), 46:460 (May 1, 2005).
Newton et al., "Inhibition of Experimental Metastasis of Human Breast Carcinoma Cells in Athymic Nude Mice by Anti-α5β1 Fibronectin Receptor Integrin Antibodies" International Journal of Oncology 6:1063-1070 (Feb. 23, 1995).
Ohno et al., "Antigen-Binding Specificities of Antibodies are Primarily Determined by Seven Residues of $V_H$" Proc. Nat'l. Acad. Sci. USA 82:2945-2949 ( 1985).
Orecchia et al., "Vascular Endothelial Growth Factor Receptor-1 is Deposited in the Extracellular Matrix by Endothelial Cells and is a Ligand for the α5β1 Integrin" Journal of Cell Science 116(17):3479-3489 ( 2003).
Pakula et al., "Genetic Analysis of Protein Stability and Function" Annu. Rev. Genet. 23:289-310 ( 1989).
Pan et al., "Blocking Neuropilin-1 Function Has an Additive Effect With Anti-VEGF to Inhibit Tumor Growth" Cell Press 11:53-67 (Jan. 2007).

(56) References Cited

OTHER PUBLICATIONS

Parsons-Wingerter, "Uniform Overexpression and Rapid Accessibility of α5β1 Integrin on Blood Vessels in Tumors" American Journal of Pathology 167(1):193-211 (Jul. 2005).
Ramakrishnan et al., "Preclinical Evaluation of an Anti-α5β1 Integrin Antibody as a Novel Anti-Angiogenic Agent" Journal of Experimental Therapeutic and Oncology 5(4):273-286 ( 2006).
Roitt et al., "Immunology" Moscow, 'Mir' (Translated from Russian by the McElroy Translation Company), pp. 110-111 ( 2000).
Schiller et al., Loss of the Tumorgenic Phenotype With in Vitro, But Not in Vivo, Passaging of a Novel Series of Human Bronchial Epithelial Cell Lines: Possible Role of an α5β1-Integrin—Fibronectin Interaction :, Cancer Research 55:6215-6221 (Dec. 15, 1995).
Schreiner et al., "Defective Vasculature in Fibronectin-Receptor-Deficient CHO Cell Tumors in Nude Mice" nternational Journal of Cancer 55:436-441 (Mar. 26, 1993).
Serini et al., "Integrins and Angiogenesis: A Sticky Business" Experimental Cell Research 312:651-658 ( 2006).
Shibata et al. "Fibronectin Secretion From Human Peritoneal Tissue Induces $M_r$ 92,000 Type IV Collagenase Expression and Invasion in Ovarian Cancer Cell Lines," *Cancer Research* 57:5416-5420, (Dec. 1, 1997).
Smit et al., "Role of Integrins in the Attachment of Metastatic Follicular Thyroid Carcinoma Cell Lines to Bone" Thyroid 8(1):29-36 (Jan. 1998).
Sone et al., "Neutralization of Vascular Endothelial Growth Factor Prevents Collagen-Induced Arthritis and Ameliorates Established Disease in Mice" Biochem. Biophys. Res. Commun. 281(2):562-568 (Feb. 23, 2001).
Stoeltzing et al., "Inhibition of Integrin α5β1 Function With a Small Peptide (ATN-161) Plus Continuous 5-FU Infusion Reduces Colorectal Liver Metastases and Improves Survival in Mice" Int. J. Cancer 104(4):496-503 (Apr. 20, 1993).
Summers et al., "A Conservative Amino Acid Substitution, Arginine for Lysine, Abolishes Export of a Hybrid Protein in *Escherichia coli*," J. Biol. Chem. 264(33):20082-20088 ( 1989).
Tanaka et al., "Elastic Plasma-Protein-Film Blended With Platelet-Releasate Accelerates Healing of Diabetic Mouse Skin Wounds" Blood 106(11):583A (Nov. 1, 2005).
Thorpe et al., "Selective Killing of Proliferating Vascular Endothelial Cells by an Anti-Fibronectin Receptor Immunotoxin" ((Abstract Only)), International Journal of Radiation Biology. 60(1-2): 24, 1991.
Van Der Pluijm et al., "ttachment Characteristics and Involvement of Integrins in Adhesion of Breast Cancer Cell Lines to Extracellular Bone Matrix Components" Lab. Invest. 77(6):665-675 (Dec. 1997).
Varner et al., "Integrin α5β1 Expression Negatively Regulates Cell Growth: Reversal by Attachment to Fibronectin" Mol. Biol. Cell. 6(6):725-740 (Jun. 1995).
Wark et al., "Latest Technologies for the Enhancement of Antibody Affinity" Advanced Drug Delivery Reviews 58(5):657-670 ( 2006).
Yamada et al., "Monoclonal Antibody and Synthetic Peptide Inhibitors of Human Tumor Cell Migration" 50 15:4485-4496 (Aug. 1, 1990).
International Search Report mailed on Jun. 17, 2010, for PCT Patent Application No. PCT/US2010/028291 filed on Mar. 23, 2010, six pages.
Written Opinion of the International Searching Authority mailed on Jun. 17, 2010, for PCT Patent Application No. PCT/US2010/028291 filed on Mar. 23, 2010, seven pages.
Aiello et al. "Suppression of Retinal Neovascularization in vivo by Inhibition of Vascular Endothelial Growth Factor (VEGF) Using Soluble VEGF-Receptor Chimeric Proteins," Proc. Natl. Acad. Sci. USA (Nov. 1995) 92:10457-10461.
Presta et al. "Humanization of an Anti-Vascular Endothelial Growth Factor Monoclonal Antibody for the Therapy of Solid Tumors and Other Disorders," Cancer Research (Oct. 15, 1997) 57:4593-4599.
Hoogenboom et al. "Overview of Antibody Phage-Display Technology and its Applications," Methods Mol. Biol. 178:1-37 (2002).

\* cited by examiner

FIG. 1

| FIG. 1A |
|---------|
| FIG. 1B |

FIG. 1A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | Kabat - CDR L1 | | | | |
| | | | | | | | | | | | | | | | | | | | | | | | | | | | | | Chothia - CDR L1 | | | | | | | | | |
| | | | | | | | | | | | | | | | | | | | | | | | | | | | | | | | | | Contact - CDR L1 | | | | | |
| hum lambda III | - | S | E | L | T | Q | D | - | P | A | V | S | V | A | L | G | Q | T | V | R | I | T | C | X | X | X | X | X | X | X | X | X | X | X | X | X | X | W | Y |
| Hamster 18C12 | Q | P | V | L | T | Q | S | - | P | S | A | S | A | S | L | G | N | S | V | K | I | T | C | T | L | S | S | Q | H | S | T | Y | T | I | G | W | Y |
| h18C12.v1.1 | D | I | V | L | T | Q | S | - | P | S | A | S | A | S | L | G | A | S | V | K | L | T | C | T | L | S | S | Q | H | S | T | Y | T | I | G | W | Y |
| h18C12.v3 | E | P | V | L | T | Q | S | - | P | S | A | S | A | S | L | G | A | S | V | K | L | T | C | T | L | S | S | Q | H | S | T | Y | T | I | G | W | Y |
| h18C12.v6 | E | P | V | L | T | Q | S | - | P | S | A | S | A | S | L | G | Q | T | V | R | I | T | C | T | L | S | S | Q | H | S | T | Y | T | I | G | W | Y |
| h18C12.v6.1.Lam3 | S | S | E | L | T | Q | D | - | P | A | V | S | V | A | L | G | Q | T | V | R | I | T | C | T | L | S | S | Q | H | S | T | Y | T | I | G | W | Y |
| h18C12.v6.2.Lam3 | S | S | E | L | T | Q | D | - | P | A | V | S | V | A | L | G | Q | T | V | R | I | T | C | T | L | S | S | Q | H | S | T | Y | T | I | G | W | Y |
| h18C12.v6.1.5 | S | S | E | L | T | Q | D | - | P | A | V | S | V | A | L | G | Q | T | V | R | I | T | C | T | L | S | S | Q | H | S | T | Y | T | I | G | W | Y |

| FIG. 2A |
| FIG. 2B |

FIG. 2A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | |
| | | | | | | | | | | | | | | | | | | | | | | | | | | Chothia - CDR H1 | | | | | Kabat - CDR H1 | | | | | | | | | | | |
| | | | | | | | | | | | | | | | | | | | | | | | | | | | | | | Contact - CDR H1 | | | | | | | | | | | |
| Hamster 18C12 | E | V | H | L | V | E | S | G | G | D | L | V | Q | P | G | S | S | L | K | L | S | C | A | A | S | G | F | T | F | S | N | R | W | I | Y | A | — | W | V | R | Q | A |
| hum VH III | E | V | Q | L | V | E | S | G | G | G | L | V | Q | P | G | G | S | L | R | L | S | C | A | A | S | G | X | X | X | X | X | X | X | X | X | W | N | W | V | R | Q | A |
| h18C12.v3 | E | V | Q | L | V | E | S | G | G | G | L | V | Q | P | G | G | S | L | R | L | S | C | A | A | S | G | F | T | F | S | N | R | W | I | Y | — | — | W | V | R | Q | A |
| h18C12.v6 | E | V | Q | L | V | E | S | G | G | G | L | V | Q | P | G | G | S | L | R | L | S | C | A | A | S | G | F | T | F | S | N | R | W | I | Y | — | — | W | V | R | Q | A |
| h18C12.v6.1.Lam3 | E | V | Q | L | V | E | S | G | G | G | L | V | Q | P | G | G | S | L | R | L | S | C | A | A | S | G | F | T | F | S | A | R | W | I | Y | — | — | W | V | R | Q | A |
| h18C12.v6.2.Lam3 | E | V | Q | L | V | E | S | G | G | G | L | V | Q | P | G | G | S | L | R | L | S | C | A | A | S | G | F | T | F | S | A | R | W | I | Y | — | — | W | V | R | Q | A |
| h18C12.v6.1.5 | E | V | Q | L | V | E | S | G | G | G | L | V | Q | P | G | G | S | L | R | L | S | C | A | A | S | G | F | T | F | S | A | R | W | I | Y | — | — | W | V | R | Q | A |

| Kabat# | 41 | 42 | 43 | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | Kabat - CDR H2 | | | | | | | | | | | | | | | | | | | |
| | | | | | | | | | | | | Chothia - CDR H2 | | | | | | | | | | | | | | | | | | | | | | | | | | | | | |
| | | | | | | | | | | | | | | | Contact - CDR H2 | | | | | | | | | | | | | | | | | | | | | | | | | | |
| Hamster 18C12 | P | G | K | G | L | E | W | V | G | G | I | K | | | | T | K | P | N | I | Y | A | T | E | Y | A | D | S | V | K | G | R | F | T | I | S | R | D | S | K | N | S |
| hum VH III | P | G | K | G | L | E | W | V | S | X | X | X | | | | X | X | X | X | X | X | X | A | D | S | V | K | G | R | F | T | I | S | R | D | N | S | K | N | T | L | Y |
| h18C12.v3 | P | G | K | G | L | E | W | V | G | G | I | K | | | | P | N | I | Y | A | T | E | Y | A | D | S | V | K | G | R | F | T | I | S | R | D | N | S | K | N | T | L | Y |
| h18C12.v6 | P | G | K | G | L | E | W | V | G | G | I | K | | | | P | N | I | Y | A | T | E | Y | A | D | S | V | K | G | R | F | T | I | S | R | D | D | S | K | N | T | L | Y |
| h18C12.v6.1.Lam3 | P | G | K | G | L | E | W | V | G | G | I | K | | | | P | A | I | Y | A | T | E | Y | A | D | S | V | K | G | R | F | T | I | S | R | D | D | S | K | N | T | L | Y |
| h18C12.v6.2.Lam3 | P | G | K | G | L | E | W | V | G | G | I | K | | | | P | A | I | Y | A | T | E | Y | A | D | S | V | K | G | R | F | T | I | S | R | D | D | S | K | N | T | L | Y |
| h18C12.v6.1.5 | P | G | K | G | L | E | W | V | G | G | I | K | | | | P | A | I | Y | A | T | E | Y | A | D | S | V | K | G | R | F | T | I | S | R | D | D | S | K | N | T | L | Y |

| Kabat# | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | 101 | 102 | 103 | 104 | 105 | 106 | 107 | SEQ ID NO |
|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | Kabat - CDR H3 | | | | | | | | | | | | | | |
| | | | | | | | | | | | | | | | | | | | | Chothia - CDR H3 | | | | | | | | | | | | |
| | | | | | | | | | | | | | | | | | | | | | Contact - CDR H3 | | | | | | | | | | |
| Hamster 18C12 | L | Q | M | N | E | I | R | V | D | D | T | A | I | Y | Y | C | T | S | L | T | G | M | R | Y | F | D | Y | W | G | Q | G | T | 9 |
| hum VH III | L | Q | M | N | S | L | R | A | E | D | T | A | V | Y | Y | C | A | R | X | X | X | X | X | X | X | X | X | W | G | Q | G | T | 10 |
| h18C12.v3 | L | Q | M | N | S | L | R | A | E | D | T | A | V | Y | Y | C | A | R | L | T | G | M | R | Y | F | D | Y | W | G | Q | G | T | 11 |
| h18C12.v6 | L | Q | M | N | S | L | R | A | E | D | T | A | V | Y | Y | C | A | R | L | T | G | M | K | Y | F | D | Y | W | G | Q | G | T | 12 |
| h18C12.v6.1.Lam3 | L | Q | M | N | S | L | R | A | E | D | T | A | V | Y | Y | C | A | R | L | T | G | M | K | Y | F | D | Y | W | G | Q | G | T | 13 |
| h18C12.v6.2.Lam3 | L | Q | M | N | S | L | R | A | E | D | T | A | V | Y | Y | C | A | R | L | T | G | M | K | Y | F | D | Y | W | G | Q | G | T | 13 |
| h18C12.v6.1.5 | L | Q | M | N | S | L | R | A | E | D | T | A | V | Y | Y | C | A | R | L | T | G | M | K | Y | F | D | Y | W | G | Q | G | T | 14 |

| Clone | CDR-L1 24 | 25 | 26 | 27 | A | 28 | 29 | 30 | 31 | 32 | 33 | 34 | SEQ ID No |
|---|---|---|---|---|---|---|---|---|---|---|---|---|---|
| h18C12.v3 | T | L | S | S | Q | H | S | T | Y | T | I | G | 21 |
| h18C12.v6 | T | L | S | S | Q | H | S | T | Y | T | I | G | 21 |
| h18C12.v7 | T | L | S | S | Q | H | S | T | Y | T | I | G | 21 |
| h18C12.v9 | T | L | S | P | Q | H | F | T | Y | K | I | D | 22 |
| h18C12.v15 | T | L | S | S | N | H | S | I | Y | T | I | S | 23 |
| h18C12.v16 | T | L | S | S | Q | H | S | T | Y | T | I | G | 21 |
| h18C12.v28 | T | L | T | T | Q | H | S | T | Y | T | I | G | 24 |
| h18C12.v30 | T | L | S | S | Q | H | S | T | Y | T | I | G | 21 |
| h18C12.v51 | T | L | S | S | Q | H | S | T | Y | T | I | G | 21 |
| h18C12.v54 | T | L | S | S | Q | H | S | T | Y | T | I | G | 21 |
| h18C12.v70 | T | L | S | S | Q | H | S | T | Y | T | I | G | 21 |
| h18C12.v78 | T | L | S | S | Q | H | S | T | Y | T | I | G | 21 |

| Clone | CDR-L2 50 | A | B | C | D | 51 | 52 | 53 | 54 | 55 | 56 | SEQ ID No | CDR-L3 89 | 90 | 91 | 92 | 93 | 94 | 95 | 96 | 97 | SEQ ID No |
|---|---|---|---|---|---|---|---|---|---|---|---|---|---|---|---|---|---|---|---|---|---|---|
| h18C12.v3 | L | N | S | D | G | S | H | N | K | G | D | 25 | G | S | S | Y | S | S | G | Y | V | 29 |
| h18C12.v6 | L | N | S | D | G | S | H | N | K | G | D | 25 | A | A | Y | A | Y | G | Y | V | 30 |
| h18C12.v7 | L | N | S | D | G | S | H | N | K | G | D | 25 | G | Y | S | Y | Y | S | G | Y | V | 31 |
| h18C12.v9 | L | N | S | D | G | S | H | N | K | G | D | 25 | G | S | S | Y | S | T | G | Y | V | 32 |
| h18C12.v15 | L | N | S | D | G | S | H | N | K | G | D | 25 | G | S | S | Y | S | S | G | Y | V | 29 |
| h18C12.v16 | L | N | S | D | G | S | H | N | K | G | D | 25 | G | S | S | Y | S | S | G | Y | I | 33 |
| h18C12.v28 | L | N | S | D | G | S | H | N | K | G | D | 25 | G | A | S | Y | S | S | G | Y | V | 29 |
| h18C12.v30 | L | N | S | D | G | S | H | N | K | G | D | 25 | G | S | S | Y | S | S | G | Y | V | 29 |
| h18C12.v51 | I | N | S | D | G | S | H | N | K | G | D | 25 | G | S | S | Y | S | S | G | Y | V | 29 |
| h18C12.v54 | L | T | S | H | G | L | H | Q | K | G | V | 26 | G | S | S | Y | S | S | G | Y | V | 29 |
| h18C12.v70 | L | N | S | D | S | T | Y | H | I | T | V | 27 | G | S | S | Y | S | S | G | Y | V | 29 |
| h18C12.v78 | L | N | S | D | G | S | H | Y | T | A | V | 28 | G | S | S | Y | S | S | G | Y | V | 29 |

| Clone | CDR-H1 26 | 27 | 28 | 29 | 30 | 31 | 32 | 33 | 34 | 35 | SEQ ID No |
|---|---|---|---|---|---|---|---|---|---|---|---|
| h18C12.v3 | G | F | T | F | S | N | R | W | I | Y | 34 |
| h18C12.v6 | G | F | T | F | S | N | R | W | I | Y | 34 |
| h18C12.v7 | G | F | T | F | S | N | R | W | I | Y | 34 |
| h18C12.v9 | G | F | T | F | S | N | R | W | I | Y | 34 |
| h18C12.v15 | G | F | T | F | S | N | R | W | I | Y | 34 |
| h18C12.v16 | G | F | T | F | S | N | R | W | I | Y | 34 |
| h18C12.v28 | G | F | T | F | S | N | R | W | I | Y | 34 |
| h18C12.v30 | G | F | T | F | S | N | R | W | V | Y | 35 |
| h18C12.v51 | G | F | T | F | S | N | R | W | I | Y | 34 |
| h18C12.v54 | G | F | T | F | S | N | R | W | I | Y | 34 |
| h18C12.v70 | G | F | T | F | S | N | R | W | I | Y | 34 |
| h18C12.v78 | G | F | T | F | S | N | R | W | I | Y | 34 |

| Clone | CDR-H2 50 | 51 | 52 | A | B | C | 53 | 54 | 55 | 56 | 57 | 58 | 59 | 60 | 61 | 62 | 63 | 64 | 65 | SEQ ID No |
|---|---|---|---|---|---|---|---|---|---|---|---|---|---|---|---|---|---|---|---|---|
| h18C12.v3 | G | I | K | T | K | P | N | I | Y | A | T | E | Y | A | D | S | V | K | G | 36 |
| h18C12.v6 | G | I | K | T | K | P | N | I | Y | A | T | E | Y | A | D | S | V | K | G | 36 |
| h18C12.v7 | G | I | K | T | K | P | N | I | Y | A | T | E | Y | A | D | S | V | K | G | 36 |
| h18C12.v9 | G | I | K | T | K | P | N | I | Y | A | T | E | Y | A | D | S | V | K | G | 36 |
| h18C12.v15 | G | I | K | T | K | P | N | I | Y | A | T | E | Y | A | D | S | V | K | G | 36 |
| h18C12.v16 | G | I | K | T | K | P | N | I | Y | A | T | E | Y | A | D | S | V | K | G | 36 |
| h18C12.v28 | G | I | K | T | K | P | T | I | Y | A | T | E | Y | A | D | S | V | K | G | 36 |
| h18C12.v30 | G | I | K | T | K | P | N | I | Y | R | Y | A | T | E | Y | A | D | S | V | K | G | 37 |
| h18C12.v51 | G | I | K | T | K | P | N | I | Y | A | T | E | Y | A | D | S | V | K | G | 36 |
| h18C12.v54 | G | I | K | T | K | P | N | I | Y | A | T | Q | Y | A | D | S | V | K | G | 40 |
| h18C12.v70 | G | I | K | T | K | P | N | I | Y | A | T | E | Y | A | D | S | V | K | G | 36 |
| h18C12.v78 | G | I | K | T | K | P | N | I | Y | A | T | E | Y | A | D | S | V | K | G | 36 |

| Clone | CDR-H3 95 | 96 | 97 | 98 | 99 | 100 | 101 | 102 | SEQ ID No |
|---|---|---|---|---|---|---|---|---|---|
| h18C12.v3 | L | T | G | M | R | Y | F | D | Y | 38 |
| h18C12.v6 | L | T | G | M | K | Y | F | D | Y | 39 |
| h18C12.v7 | L | T | G | M | R | Y | F | D | Y | 38 |
| h18C12.v9 | L | T | G | M | R | Y | F | D | Y | 38 |
| h18C12.v15 | L | T | G | M | R | Y | F | D | Y | 38 |
| h18C12.v16 | L | T | G | M | R | Y | F | D | Y | 38 |
| h18C12.v28 | V | T | G | M | R | Y | F | D | Y | 40 |
| h18C12.v30 | L | T | G | M | R | Y | F | D | Y | 38 |
| h18C12.v51 | L | T | G | M | R | Y | F | D | Y | 39 |
| h18C12.v54 | L | T | G | M | R | Y | F | D | Y | 38 |
| h18C12.v70 | L | T | G | M | R | Y | F | D | Y | 38 |
| h18C12.v78 | L | T | G | M | R | Y | F | D | Y | 38 |

| Anti-α5β1 hIgG BIAcore Analysis (Ligand: hIgG; Analyte: α5β1) | | | |
|---|---|---|---|
| Anti-α5β1 | Human Integrin α5β1 (R&D) | | |
| | kon(10$^5$ M$^{-1}$S$^{-1}$) | koff(10$^{-4}$ S$^{-1}$) | Kd(nM) |
| h18C12.v3 | 0.71 ± 0.08 | 8.07 ± 0.37 | 11.5 ± 1.1 |
| h18C12.v6 | 1.74 ± 0.51 | 7.50 ± 1.64 | 4.8 ± 2.1 |
| h18C12.v15 | 2.23 ± 0.09 | 15.2 ± 0.5 | 6.9 ± 0.3 |
| h18C12.v54 | 0.63 ± 0.11 | 7.34 ± 0.32 | 11.9 ± 2.4 |
| h18C12.v70 | 0.66 ± 0.19 | 12.8 ± 0.8 | 20.3 ± 3.8 |

*FIG. 5*

| Anti-α5β1 hIgG BIAcore Summary (Ligand: hIgG; Analyte: α5β1) | | | |
|---|---|---|---|
| Antibody | Human Integrin α5β1 (R&D) | | |
| | kon(10$^5$ M$^{-1}$S$^{-1}$) | koff(10$^{-4}$ S$^{-1}$) | Kd(nM) |
| h18C12.v6.1.Lam3 | 0.97 ± 0.03 | 3.86 ± 0.24 | 4.00 ± 0.32 |
| Chimeric 18C12 | 1.2 ± 0.1 | 9.22 ± 0.19 | 7.68 ± 0.53 |

*FIG. 6*

| Anti-α5β1 h18C12.v6.1 Variants | CDR-L2 | | | | Human Integrin α5β1 (R&D) | | |
|---|---|---|---|---|---|---|---|
| | 50a | 50b | 50c | 50d | kon(10$^5$ M$^{-1}$S$^{-1}$) | koff(10$^{-4}$ S$^{-1}$) | Kd(nM) |
| h18C12.v6.1.1 | S | S | S | G | 1.2 | 32 | 26.7 |
| h18C12.v6.1.2 | N | S | D | G | 0.48 | 6.43 | 13.5 |
| h18C12.v6.1.3 | N | S | A | G | 1.1 | 40 | 36.4 |
| h18C12.v6.1.4 | N | S | D | A | 0.46 | 14.4 | 31.6 |
| h18C12.v6.1.5 | N | S | D | S | 0.43 | 6.59 | 15.5 |

ANTI-α5β1 ANTIBODIES AND USES THEREOF

CROSS-REFERENCE TO RELATED APPLICATIONS

This application is a continuation of U.S. application Ser. No. 12/729,999, filed Mar. 23, 2010 now U.S. Pat. No. 8,124,740, which claims the benefit of U.S. Provisional Patent Application No. 61/163,241, filed Mar. 25, 2009, the disclosures of which is incorporated by reference in their entirety for all purposes.

FIELD OF THE INVENTION

The present invention relates to novel $\alpha_5\beta_1$ antibodies, compositions and kits comprising the antibodies and methods for using the antibodies.

BACKGROUND OF THE INVENTION

α5β1 integrin is a cell membrane glycoprotein that mediates cell-ECM interactions through its major ligand, fibronectin. α5β1 integrin plays a role in cell migration, differentiation and survival. Levels of α5β1 integrin are elevated in tumor vascular endothelium (e.g., gastric, colorectal hepatocellular, uterocervial, and breast carcinomas) and other angiogenic vessels. α5β1 integrin modulates mural cell association with endothelial cells and the assembly of the endothelial extracellular matrix during angiogenesis. As such, α5β1 integrin is a useful target for inhibition of angiogenesis and sensitization of cells to the effects of a VEGF antagonist.

Thus, there is a need in the art for compositions and methods for targeting α5β1 integrin. The present invention meets this and other needs.

SUMMARY OF THE INVENTION

The present invention provides novel anti-$\alpha_5\beta_1$ antibodies derived from the monoclonal antibody 18C12, kits and compositions comprising the novel anti-$\alpha_5\beta_1$ antibodies, and methods of making and/or using them.

One embodiment of the invention provides an anti-$\alpha_5\beta_1$ antibody comprising a VL domain comprising a CDR-L1 comprising TL-S/T-S/P/T-Q/N-H-F/S-T/I-Y-K/T-I-G/D/S (SEQ ID NO:15); a CDR-L2 comprising L/I-N/T-S-D/H/S-G/S-S/L/T-H/Y-N/K/Q/I-K/T-G/A-D/S/V (SEQ ID NO:16); a CDR-L3 comprising G/A-S/A/Y-S/Y-Y-S/A/Y-S/Y/T-GY-V/I (SEQ ID NO:17); and a VH domain comprising a CDR-H1 comprising GFTFS-N/A-RW-I/V-Y (SEQ ID NO:18); a CDR-H2 comprising GIKTKP-N/A/T-I/R-YAT-E/Q-YADS-VKG (SEQ ID NO:19); and a CDR-H3 comprising L/V-TG-M/K-R/K-YFDY (SEQ ID NO:20). In some embodiments, the anti-$\alpha_5\beta_1$ antibody comprises a VL domain comprising a CDR-L1, CDR-L2, and CDR-L3 each comprising a sequence set forth in FIG. 3 and a VH domain comprising a CDR-H1, CDR-H2, and CDR-H3 each comprising a sequence set forth in FIG. 3, i.e., a VL domain comprising a CDR-L1 comprising a sequence set forth in SEQ ID NO: 21, 22, 23, or 24, a CDR-L2 comprising a sequence set forth in SEQ ID NO: 25, 26, 27, or 28, and a CDR-L3 comprising a sequence set forth in SEQ ID NO: 29, 30, 31, 32 or 33; and a VH domain comprising a CDR-H1 comprising a sequence set forth in SEQ ID NO: 34 or 35, a CDR-H2 comprising a sequence set forth in SEQ ID NO: 36 or 37, and a CDR-H3 comprising a sequence set forth in SEQ ID NO: 38, 39, or 40. In some embodiments, the anti-$\alpha_5\beta_1$ antibody comprises a VL domain comprising any one of SEQ ID NOS:3-8 and a VH domain comprising any one of SEQ ID NOS:11-14. In some embodiments, the anti-$\alpha_5\beta_1$ antibody comprises a VL domain comprising SEQ ID NO:4 and a VH domain comprising SEQ ID NO:11. In some embodiments, the anti-$\alpha_5\beta_1$ antibody comprises a VL domain comprising SEQ ID NO:5 and a VH domain comprising SEQ ID NO:12. In some embodiments, the anti-$\alpha_5\beta_1$ antibody comprises a VL domain comprising SEQ ID NO:6 and a VH domain comprising SEQ ID NO:13. In some embodiments, the anti-$\alpha_5\beta_1$ antibody comprises a VL domain comprising SEQ ID NO:7 and a VH domain comprising SEQ ID NO:13. In some embodiments, the anti-$\alpha_5\beta_1$ antibody comprises a VL domain comprising SEQ ID NO:8 and a VH domain comprising SEQ ID NO:14. In some embodiments, the anti-$\alpha_5\beta_1$ antibody is human, humanized or chimeric. In one embodiment, the anti-$\alpha_5\beta_1$ antibody is a monoclonal antibody. In some embodiments, the anti-$\alpha_5\beta_1$ antibody competes with the 18C12 antibody for binding to $\alpha_5\beta_1$ integrin. In some embodiments, the monoclonal antibody is a chimeric antibody. In some embodiments, the anti-$\alpha_5\beta_1$ antibody is an antibody fragment that binds $\alpha_5\beta_1$. In some embodiments, the anti-$\alpha_5\beta_1$ antibody is selected from: a Fab, Fab', a F(ab)'$_2$, single-chain Fv (scFv), an Fv fragment; a diabody and a linear antibody. In some embodiments, the anti-$\alpha_5\beta_1$ antibody is a full length IgG1 or a full length IgG4. In some embodiments, the anti-$\alpha_5\beta_1$ antibody is a bispecific antibody or a multispecific antibody. In some embodiments, the bispecific antibody binds VEGF and $\alpha_5\beta_1$ and is a VEGF antagonist. In some embodiments, the anti-$\alpha_5\beta_1$ antibody has an altered effector function. In some embodiments, the anti-$\alpha_5\beta_1$ antibody is altered to decrease or prevent antibody dependent cellular cytotoxicity (ADCC) or complement dependent cytotoxicity (CDC) activity (e.g., by altering the nucleic acid sequence encoding the Fc portion of the antibody). In some embodiments, the Fc portion of the antibody comprises a N297A substitution. In some embodiments, the anti-$\alpha_5\beta_1$ antibody has been modified to increase or decrease its half-life in humans (e.g., by altering the nucleic acid sequence encoding the Fc portion of the antibody). In some embodiment, the $\alpha_5\beta_1$ antibody is part of an an immunoonjugate conjugated to another entity (e.g., a therapeutic agent or a detectable label). In some embodiments, the therapeutic entity is a cytotoxic agent (e.g., radioactive isotope, a toxin, a growth-inhibitory agent, or a chemotherapeutic agent). In some embodiments, the detectable label is a fluorescent dye, a radioisotope, or an enzyme.

Further embodiments of the invention provide nucleic acid molecules encoding any of the anti-$\alpha_5\beta_1$ antibodies described herein, expression vectors comprising the nucleic acids, and host cells comprising the nucleic acids. Yet further embodiments of the invention provide methods of producing any of the anti-$\alpha_5\beta_1$ antibodies described herein, the methods comprising culturing the host cells so that the antibody is produced. In some embodiments, the methods further comprise recovering the antibody from the host cell.

Additional embodiments of the invention provide pharmaceutical compositions comprising a $\alpha_5\beta_1$ antibody of this invention and a pharmaceutically acceptable carrier. In some embodiments, the pharmaceutical compositions further comprise at least one, two, three, four, or more additional agent(s) including, e.g., a VEGF antagonist. In some embodiments, the additional agent(s) are selected from a cytotoxic agent, a chemotherapeutic agent, a growth-inhibitory agent, or an anti-angiogenic agent. In some embodiments, the VEGF antagonist is an anti-VEGF antibody. In some embodiments, the anti-VEGF antibody is bevacizumab. The invention also provides articles of manufacture and kits comprising instructions for detecting $\alpha_5\beta_1$ (e.g., in a subject who has been treated with a VEGF antagonist).

Another embodiment of the invention provides methods of treating subjects suffering from a disease or disorder involving abnormal angiogenesis, vascular permeability, or vascular leakage. The methods comprising administering a therapeutically effective amount of the anti-$\alpha_5\beta_1$ antibodies described herein to the subject, thereby treating the disease or disorder (e.g., by partially or completely inhibiting abnormal angiogenesis, vascular permeability, or vascular leakage). In some embodiments, a VEGF antagonist is also administered to the subject. In some embodiments, the VEGF antagonist and the anti-$\alpha_5\beta_1$ antibody are administered concurrently. In some embodiments, the VEGF antagonist and the anti-$\alpha_5\beta_1$ antibody are administered sequentially. In some embodiments, the disease or disorder is responsive to VEGF antagonist therapies. In some embodiments, the disease or disorder is selected from: a cancer, an immune disease or an ocular disease. According to one embodiment, the disease or disorder is selected from: a solid tumor, a metastatic tumor, a soft tissue tumor, a disease having ocular neovascularisation, an inflammatory disease having abnormal angiogenesis, a disease arising after transplantation into the subject and a disease having abnormal proliferation of fibrovascular tissue. According to another embodiment, the cancer is selected from: breast cancer (including metastatic breast cancer), cervical cancer, colorectal cancer (including metastatic colorectal cancer), lung cancer (including non-small cell lung cancer), non-Hodgkins lymphoma (NHL), chronic lymphocytic leukemia, renal cell cancer, prostate cancer including hormone refractory prostate cancer, liver cancer, head and neck cancer, melanoma, ovarian cancer, mesothelioma, soft tissue cancer, gastrointestinal stromal tumor, glioblastoma multiforme and multiple myeloma. According to another embodiment, the disease is selected from: retinopathy, age-related macular degeneration (e.g., wet AMD), diabetic macular edema, retinal vein occlusion (RVO), and dry AMD/geographic atrophy (for prevention of progression to wet AMD) rubeosis; psoriasis, an inflammatory renal disease, haemolytic uremic syndrome, diabetic nephropathy (e.g., proliferative diabetic retinopathy), arthritis (e.g., psoriatic arthritis, osteoarthritis, rheumatoid arthritis), inflammatory bowel disease, chronic inflammation, chronic retinal detachment, chronic uveitis, chronic vitritis, corneal graft rejection, corneal neovascularization, corneal graft neovascularization, Crohn's disease, myopia, ocular neovascular disease, Pagets disease, pemphigoid, polyarteritis, post-laser radial keratotomy, retinal neovascularization, Sogrens syndrome, ulcerative colitis, graft rejection, lung inflammation, nephrotic syndrome, edema, ascites associated with malignancies, stroke, angiofibroma and neovascular glaucoma. In one embodiment, the methods further comprise administering an additional therapeutic agent (e.g., an anti-neoplastic agent, a chemotherapeutic agent, a growth inhibitory agent, or a cytotoxic agent) to the subject.

Yet another embodiment of the invention provides methods of treating cancer in a subject, the methods comprising: administering therapeutically effective amount of a VEGF antagonist and an anti-$\alpha_5\beta_1$ antibody to the subject. In some embodiments, the VEGF antagonist and the anti-$\alpha_5\beta_1$ antibody are administered concurrently. In some embodiments, the VEGF antagonist and the anti-$\alpha_5\beta_1$ antibody are administered sequentially. In some embodiments, the cancer is responsive to VEGF antagonist therapies.

A further embodiment of the invention provides methods of treating age related macular degeneration (AMD) (including, e.g., wet age-related macular degeneration) in a subject suffering from AMD, the methods comprising: administering a therapeutically effective amount of a VEGF antagonist and an anti-$\alpha_5\beta_1$ antibody to the subject. In some embodiments, the VEGF antagonist and the anti-$\alpha_5\beta_1$ antibody are administered concurrently. In some embodiments, the VEGF antagonist and the anti-$\alpha_5\beta_1$ antibody are administered sequentially. In yet another embodiment, a method of treating an autoimmune disease in a subject comprising the step of administering a therapeutically effective amount of a VEGF antagonist and an $\alpha_5\beta_1$ antagonist concurrently or sequentially is provided.

In some embodiments, the VEGF antagonist is initially administered to the subject to be treated and the anti-$\alpha_5\beta_1$ antibody is subsequently administered to the subject. In some embodiments, the VEGF antagonist and the $\alpha_5\beta_1$ antagonist are administered to the subject simultaneously. In some embodiments, the anti-$\alpha_5\beta_1$ antibody VEGF antagonist is initially administered to the subject to be treated and the VEGF antagonist is subsequently administered to the subject. In some embodiments, the subject is treated with the VEGF antagonist until the subject is unresponsive to VEGF antagonist treatment and then the subject is treated with the anti-$\alpha_5\beta_1$ antibody. In one particular embodiment, the subject is treated with the VEGF antagonist when the cancer is non-invasive or early stage and treated with the anti-$\alpha_5\beta_1$ antibody when the cancer is invasive. In another embodiment, subject being treated with the anti-$\alpha_5\beta_1$ antibody has elevated $\alpha_5\beta_1$ levels in a diseased tissue compared to tissue from a subject not suffering from the disease or compared to non-diseased tissue. In this instance, the method can further include the step of detecting $\alpha_5\beta_1$ in the subject, e.g., in a diseased tissue after treatment with a VEGF antagonist. According to one embodiment, the invasive cancer is a metastasized cancer. According to another embodiment, the early stage cancer is a cancer treated by adjuvant therapy (e.g., chemotherapy or surgical removal).

According to one embodiment of this invention, the subject to be treated with an anti-$\alpha_5\beta_1$ antibody is suffering from a relapse after VEGF antagonist treatment or has become refractory to VEGF antagonist treatment. According to another embodiment, the subject to be treated with an anti-$\alpha_5\beta_1$ antibody and a VEGF antagonist is suffering from a metastatic cancer or has previously been treated with adjuvant therapy. In one embodiment, the candidate patient is relapsed, refractory or resistant to a chemotherapeutic agent such as irinotecan. Examples of such diseases, include but are not limited to, metastatic colorectal cancer, relapsed metastatic colorectal cancer, metastatic breast cancer, relapsed metastatic breast cancer, metastatic HER2⁺ breast cancer, adjuvant breast cancer, adjuvant HER2⁺ breast cancer, metastatic pancreatic cancer, adjuvant colon cancer, adjuvant non-small cell lung cancer, adjuvant rectal cancer, adjuvant non small cell lung cancer, metastatic non small cell lung cancer, metastatic ovarian cancer, metastatic renal cell cancer and adjuvant renal cell cancer.

According to one embodiment, the subject suffering from a disease described herein is administered a maintenance therapy after treatment for the disease with a VEGF antagonist, wherein the maintenance therapy is an $\alpha_5\beta_1$ antagonist alone or sequentially or concurrently with a VEGF antagonist.

In some embodiments, the VEGF antagonist is selected from: an antibody, an immunoadhesin, a peptibody, a small molecule and a nucleic acid that hybridizes to a nucleic acid molecule encoding VEGF under stringent conditions (e.g., ribozyme, siRNA and aptamer). In some embodiments, the VEGF antagonist is an antibody (e.g., a monoclonal antibody). According to one embodiment, the anti-VEGF antibody is capable of being competitively inhibited from binding to human VEGF by the Avastin® antibody. According to another embodiment, the anti-VEGF antibody is human, humanized or chimeric. According one specific embodiment, the anti-VEGF antibody is the Avastin® antibody. According to another embodiment, the anti-VEGF antibody is selected from the group consisting of a Fab, Fab', a F(ab)'$_2$, single-chain Fv (scFv), an Fv fragment; a diabody and a linear antibody. According to another embodiment, the VEGF antagonist is a bispecific antibody that binds both VEGF and $\alpha_5\beta_1$ and is also a $\alpha_5\beta_1$ antagonist.

A further embodiment of the invention provides methods of detecting $\alpha_5\beta_1$ protein in a sample suspected of containing the $\alpha_5\beta_1$ protein. The methods comprising (1) contacting the antibodies described herein with the sample; and detecting formation of a complex between the anti-$\alpha_5\beta_1$ antibody and the $\alpha_5\beta_1$ protein. In some embodiments, the sample is from a patient diagnosed with a disease characterized by abnormal angiogenesis, abnormal vascular permeability, and/or vascular leakage.

These and other embodiments of the invention are further described in the detailed description that follows.

BRIEF DESCRIPTION OF THE DRAWINGS

FIGS. 1A and 1B depict alignment of sequences of light-chain variable domains for the following: Human lambda III; Hamster 18C12; chimeric 18C12.v.1.1; h18C12.v3; h18C12.v6; h18C12.v6.1.Lam3; h18C12.v6.2Lam3; and h18C12.v6.1.5.

FIGS. 2A and 2B depict alignment of sequences of the heavy-chain variable domain for the following: Hamster 18C12; h18C12.v3; h18C12.v6; h18C12.v6.1.Lam3; h18C12.v6.2Lam3; and h18C12.v6.1.5.

FIG. 3 depicts CDR sequences of h18C12.v3 and h18C12.v3 affinity matured variants h18C12.v6; h18C12.v7; h18C12.v9; h18C12.v15; h18C12.v16; h18C12.v28; h18C12.v30; h18C12.v51; h18C12.v54; h18C12.v70; and h18C12.v78.

FIG. 5 depicts the results of a BIACORE® analysis of binding of h18C12.v3 parental clone and h18C12.v3 affinity matured variants h18C12.v6; h18C12.v15; h18C12.v54; and h18C12.v70 to human α5β1 integrin.

FIG. 6 depicts the results of a BIACORE® analysis of binding of chimeric 18C12 and h18C12.v6.1.Lam3 to human $\alpha_5\beta_1$ integrin.

FIG. 7 depicts the results of a BIACORE® analysis of binding of h18C12.v6.1 clones h18C12.v6.1.1, h18C12.v6.1.2, h18C12.v6.1.3, h18C12.v6.1.4, and h18C12.v6.1.5 and sets forth the CDR-L2 sequence at positions 50a, 50b, 50c, and 50d for each of the h18C12.v6.1 clones

DETAILED DESCRIPTION OF THE INVENTION

I. Introduction

Figure 4:
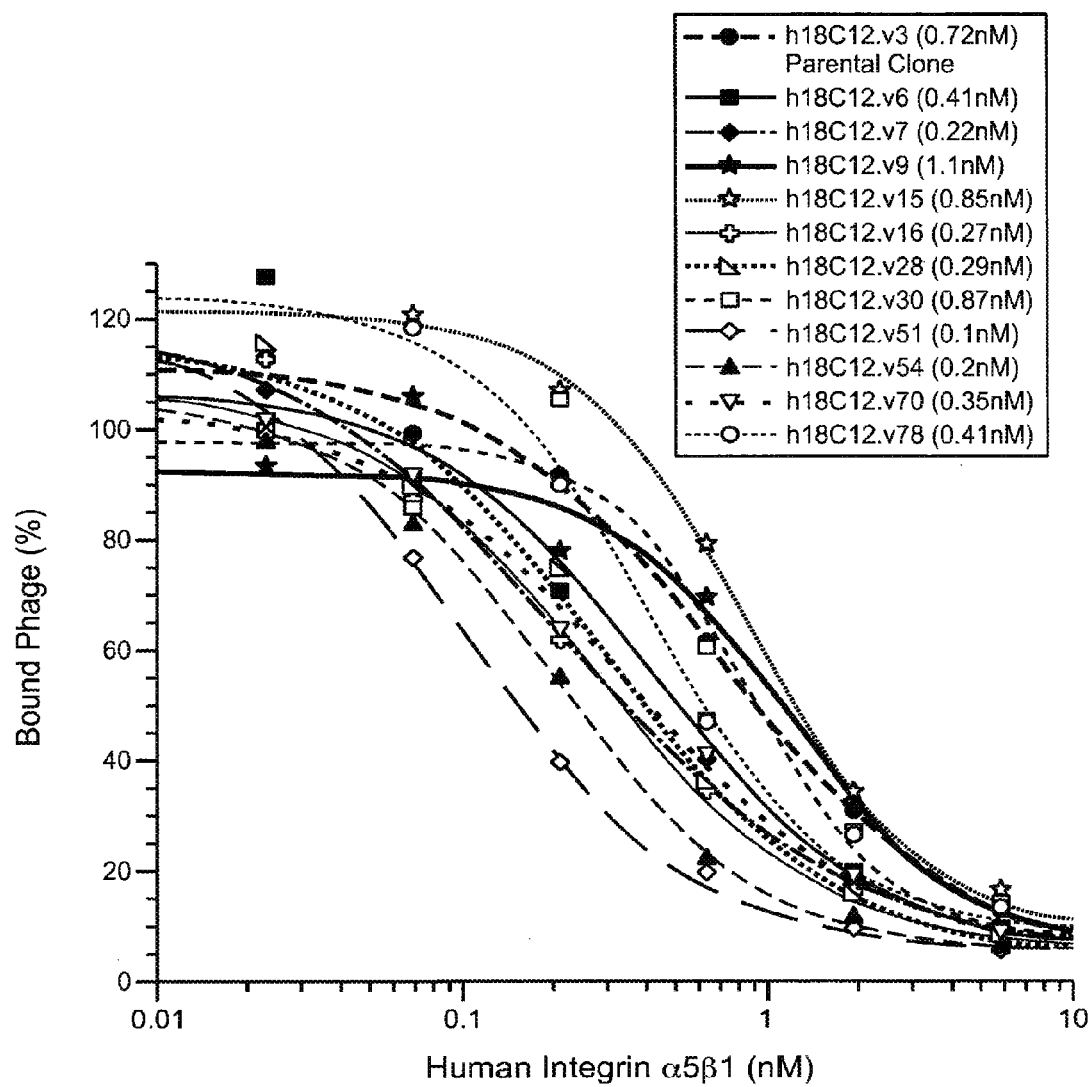
FIG. 4 depicts the results of a phage competition ELISA demonstrating binding of h18C12.v3 parental clone, and 18C12 affinity matured variants h18C12.v6; h18C12.v7; h18C12.v9; h18C12.v15; h18C12.v16; h18C12.v28; h18C12.v30; h18C12.v51; h18C12.v54; h18C12.v70; and h18C12.v78 to human $\alpha_5\beta_1$ integrin.

The present invention is based on the identification of novel antibodies that bind $\alpha_5\beta_1$ integrin. The $\alpha_5\beta_1$ antibodies are derived from the monoclonal antibody 18C12 and can be used in a variety of therapeutic and diagnostic methods. For example, the $\alpha_5\beta_1$ antibodies can be used alone or in combination with other agents for treating abnormal angiogenesis, neoplasia, ocular diseases and autoimmune diseases. The antibodies can also be used for detecting $\alpha_5\beta_1$ protein in patients or patient samples by administering the antibodies to $\alpha_5\beta_1$ protein in patients and detecting the anti-$\alpha_5\beta_1$ antibody bound to the $\alpha_5\beta_1$ protein in a sample from the patient (e.g., in vivo or ex vivo) or by contacting the antibodies with samples from patients and detecting qualitatively or quantitatively the anti-$\alpha_5\beta_1$ antibody bound to the $\alpha_5\beta_1$ protein.

II. Definitions

"Alpha5beta1" or "α5β1" or "a5b1" or "$\alpha_5\beta_1$" is an integrin comprising two different proteins (i.e., subunits Alpha5 and beta1). α5β1 has been shown to bind to fibronectin, L1-CAM and fibrinogen. α5β1 integrin is also known as Very Late Activation-5, VLA-5, alpha5beta1, CD49e/CD29, fibronectin receptor, FNR and GPIc-IIa. According to a embodiment, the α5β1 is a human α5β1.

"Alpha5" is used herein interchangeably with CD49e, α5, integrin alpha5 subunit, VLA-5 alpha subunit, IC subunit of GPIc-IIa and FNR alpha chain refers to one subunit of the $\alpha_5\beta_1$ integrin. Alpha5 has four isoforms generated by alternative splicing (A-D) and which vary within their cytoplasmic domains. Amino acid sequences for human isoforms of alpha5 can be found at, e.g., Genbank accession numbers: X07979, U33879, U33882 and U33880, respectively.

"Beta1" also called CD29, beta1, Platelet GPIIa; VLA-beta chain; beta-1 integrin chain, CD29; FNRB; MDF2; VLAB; GPIIA; MSK12 and VLA5B. Amino acid sequences for human Beta1 can be found, e.g., at Genbank Accession No. X06256.

The term "VEGF" as used herein refers to the 165-amino acid human vascular endothelial cell growth factor and related 121-, 189-, and 206-amino acid human vascular endothelial cell growth factors, as described by Leung et al. *Science*, 246:1306 (1989), and Houck et al. *Mol. Endocrin.*, 5:1806 (1991), together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. According to a embodiment, the VEGF is a human VEGF.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. Preferably, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction (e.g., immunoadhesins, peptibodies), anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor (e.g., RNAi). According to one embodiment, the VEGF antagonist binds to VEGF and inhibits VEGF-induced endothelial cell proliferation in vitro. According to one embodiment, the VEGF antagonist binds to VEGF or a VEGF receptor with greater affinity than a non-VEGF or non-VEGF receptor. According to one embodiment, the VEG antagonist binds to VEGF or a VEGF receptor with a Kd of between 1 μM and 1 pM. According to another embodiment, the VEGF antagonist binds to VEGF or a VEGF receptor between 500 nM and 1 pM.

According a embodiment, the VEGF antagonist is selected from the group consisting of a polypeptide such as an antibody, a peptibody, an immunoadhesin, a small molecule or an aptamer. In a embodiment, the antibody is an anti-VEGF antibody such as the AVASTIN® antibody or an anti-VEGF receptor antibody such as an anti-VEGFR2 or an anti-VEGFR3 antibody. Other examples of VEGF antagonists include: VEGF-Trap, Mucagen, PTK787, SU11248, AG-013736, Bay 439006 (sorafenib), ZD-6474, CP632, CP-547632, AZD-2171, CDP-171, SU-14813, CHIR-258, AEE-788, SB786034, BAY579352, CDP-791, EG-3306, GW-786034, RWJ-417975/CT6758 and KRN-633.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) Cancer Res. 57:4593-4599, including but not limited to the antibody known as bevacizumab (BV; Avastin®). According to another embodiment, anti-VEGF antibodies that can be used include, but are not limited to the antibodies disclosed in WO 2005/012359. According to one embodiment, the anti-VEGF antibody comprises the variable heavy and variable light region of any one of the antibodies disclosed in FIGS. 24, 25, 26, 27 and 29 of WO 2005/012359 (e.g., G6, G6-23, G6-31, G6-23.1, G6-23.2, B20, B20-4 and B20.4.1). In another embodiment, the anti-VEGF antibody known as ranibizumab is the VEGF antagonist administered for ocular disease such as diabetic retinopathy and wet AMD.

The anti-VEGF antibody "Bevacizumab (BV)", also known as "rhuMAb VEGF" or "Avastin®", is a recombinant humanized anti-VEGF monoclonal antibody generated according to Presta et al. (1997) Cancer Res. 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Other anti-VEGF antibodies include the antibodies described in U.S. Pat. No. 6,884,879 and WO 2005/044853.

The anti-VEGF antibody Ranibizumab or the LUCENTIS® antibody or rhuFab V2 is a humanized, affinity-matured anti-human VEGF Fab fragment. Ranibizumab is produced by standard recombinant technology methods in E. coli expression vector and bacterial fermentation. Ranibizumab is not glycosylated and has a molecular mass of ~48,000 daltons. See WO98/45331 and U.S. 2003/0190317.

Molecules, such as antibodies, characterized by binding to overlapping or the similar areas on a target can be identified by competitive inhibition/binding assays.

In one embodiment, HUVEC or other cells expressing $\alpha_5\beta_1$ are used in a competitive inhibition assay and FACS is used to evaluate binding localities of two anti-$\alpha_5\beta_1$ antibodies relative to each other. For example, HUVEC cells can be washed in conical tube and spun 5 min @ 1000 rpm. The pellet is typically washed two times. Then, the cells can be resuspended, counted and kept on ice until use. 100 μl of a first anti-$\alpha_5\beta_1$ antibody (e.g., start at a 1 μg/ml concentration or lower concentration) can be added to the well. Next, 100 μl (e.g., 20×10$^5$ cells) of cells can be added into per well and incubated on ice for 30 min. Next, 100 μl of a biotinylated anti-$\alpha_5\beta_1$ antibody (5 μg/ml stock) can be added to each well and incubated on ice for 30 min. The cells are then washed and pelleted for 5 min. @ 1000 rpm. The supernatant is aspirated. R-Phycoerythrin conjugated streptavidin (Jackson 016-110-084) is added to the well (100 μl @ 1:1000). Next, the plate can be wrapped in foil and incubated on ice 30 min. Following the incubation, the pellet can be washed and pelleted 5 min. @ 1000 rpm. The pellet can be resuspended ant transferred to microtiter tubes for FACS analysis.

An "angiogenic factor or agent" is a growth factor or its receptor which is involved in stimulating the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family and their receptors (VEGF-B, VEGF-C, VEGF-D, VEGFR1, VEGFR2 and VEGFR3), PlGF, PDGF family, fibroblast growth factor family (FGFs), TIE ligands (Angiopoietins, ANGPT1, ANGPT2), TIE1, TIE2, ephrins, Bv8, Delta-like ligand 4 (DLL4), Del-1, fibroblast growth factors: acidic (aFGF) and basic (bFGF), FGF4, FGF9, BMP9, BMP10, Follistatin, Granulocyte colony-stimulating factor (G-CSF), GM-CSF, Hepatocyte growth factor (HGF)/scatter factor (SF), Interleukin-8 (IL-8), CXCL12, Leptin, Midkine, neuropilins, NRP1, NRP2, Placental growth factor, Platelet-derived endothelial cell growth factor (PD-ECGF), Platelet-derived growth factor, especially PDGF-BB, PDGFR-alpha, or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Alk1, CXCR4, Notch1, Notch4, Sema3A, Sema3C, Sema3F, Robo4, etc. It would further include factors that promote angiogenesis, such as ESM1 and Perlecan. It would also include factors that accelerate wound healing, such as growth hormone, insulin-like growth factor-I (IGF-I), VIGF, epidermal growth factor (EGF), EGF-like domain, multiple 7 (EGFL7), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenic inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., antibodies to VEGF-A or to the VEGF-A receptor (e.g., KDR receptor or Flt-1 receptor), anti-PDGFR inhibitors, small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogenic agents include, but are not limited to, the following agents: VEGF inhibitors such as a VEGF-specific antagonist, EGF inhibitor, EGFR inhibitors, Erbitux® (cetuximab, ImClone Systems, Inc., Branchburg, N.J.), Vectibix® (panitumumab, Amgen, Thousand Oaks, Calif.), TIE2 inhibitors, IGF1R inhibitors, COX-II (cyclooxygenase II) inhibitors, MMP-2 (matrix-metalloproteinase 2) inhibitors, and MMP-9 (matrix-metalloproteinase 9) inhibitors, CP-547,632 (Pfizer Inc., NY, USA), Axitinib (Pfizer Inc.; AG-013736), ZD-6474 (AstraZeneca), AEE788 (Novartis), AZD-2171), VEGF Trap (Regeneron/Aventis), Vatalanib (also known as PTK-787, ZK-222584: Novartis & Schering A G), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof. Other angiogenesis inhibitors include thrombospondin1, thrombospondin2, collagen IV and collagen XVIII. VEGF inhibitors are disclosed in U.S. Pat. Nos. 6,534,524 and 6,235,764, both of which are incorporated in their entirety for all purposes. Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "anti-angiogenic therapy" refers to a therapy useful for inhibiting angiogenesis which comprises the administration of an anti-angiogenic agent.

The "Kd" or "Kd value" for an antibody an anti-VEGF antibody according to this invention is in one embodiment measured by a radiolabeled VEGF binding assay (RIA) performed with the Fab version of the antibody and a VEGF molecule as described by the following assay that measures solution binding affinity of Fabs for VEGF or by equilibrating Fab with a minimal concentration of ($^{125}$I)-labeled molecule VEGF(109) in the presence of a titration series of unlabeled VEGF, then capturing bound VEGF with an anti-Fab antibody-coated plate (Chen, et al., (1999) *J. Mol. Biol* 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]VEGF(109) are mixed with serial dilutions of a Fab of interest, (e.g., Fab-12 (Presta et al., (1997) *Cancer Res.* 57:4593-4599)). The Fab of interest is then incubated overnight; however, the incubation may continue for 65 hours to insure that equilibrium is reached. Thereafter, the mixtures are transferred to the capture plate for incubation at room temperature for one hour. The solution is then removed and the plate washed eight times with 0.1% Tween-20 in PBS. When the plates had dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized target molecule hVEGF (8-109) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Human VEGF is diluted with 10 mM sodium acetate, pH 4.8, into 5 µg/ml (~0.2 µM) before injection at a flow rate of 5 µl/minute to achieve approximately 10 response units (RU) of coupled protein. Following the injection of human VEGF, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate is can be determined by using a fluorescent quenching technique that measures the increase or decrease in fluorescence emission intensity (excitation=295 nm; emission=340 nm, 16 nm band-pass) at 25° C. of a 20 nM anti-VEGF antibody (Fab form) in PBS, pH 7.2, in the presence of increasing concentrations of human VEGF short form (8-109) or mouse VEGF as measured in a spectrometer, such as a stop-flow equipped spectrophotometer (Aviv Instruments) or a 8000-series SLM-Aminco spectrophotometer (ThermoSpectronic) with a stirred cuvette. Similar binding assays can be performed for determining the Kd of an anti-α5β1 Fab or antibody using α5β1 as the target.

As used herein, a subject to be treated is a mammal (e.g., human, non-human primate, rat, mouse, cow, horse, pig, sheep, goat, dog, cat, etc.). The subject may be a clinical patient, a clinical trial volunteer, an experimental animal, etc. The subject may be suspected of having or at risk for having a cancer, an immune disease, or any other disease having abnormal angiogenesis, be diagnosed with a cancer, immune disease, or any other disease having abnormal angiogenesis. Many diagnostic methods for cancer, immune disease or any other disease exhibiting abnormal angiogenesis and the clinical delineation of those diseases are known in the art. According to one embodiment, the subject to be treated according to this invention is a human.

"Abnormal angiogenesis" occurs when new blood vessels grow either excessively or otherwise inappropriately (e.g., the location, timing, degree, or onset of the angiogenesis being undesired from a medical standpoint) in a diseased state or such that it causes a diseased state. In some cases, excessive, uncontrolled, or otherwise inappropriate angiogenesis occurs when there is new blood vessel growth that contributes to the worsening of the diseased state or cause of a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-related macular degeneration, choroidal neovascularization (CNV), diabetic macular edema, pathological myopia, von Hippel-Lindau disease, histoplasmosis of the eye, Central Retinal Vein Occlusion (CRVO), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various imflammatory diseases, such as arthritis, especially rheumatoid arthritis, inflammatory bowel disease, psorsasis, sarcoidosis, arterial arteriosclerosis and diseases occurring after transplants, endometriosis or chronic asthma and more than 70 other conditions. The new blood vessels can feed the diseased tissues, destroy normal tissues, and in the case of cancer, the new vessels can allow tumor cells to escape into the circulation and lodge in other organs (tumor metastases). The present invention contemplates treating those patients that are at risk of developing the above-mentioned illnesses.

"Abnormal vascular permeability" occurs when the flow of fluids, molecules (e.g., ions and nutrients) and cells (e.g., lymphocytes) between the vascular and extravascular compartments is excessive or otherwise inappropriate (e.g., the location, timing, degree, or onset of the vascular permeability being undesired from a medical standpoint) in a diseased state or such that it causes a diseased state. Abnormal vascular permeability may lead to excessive or otherwise inappropriate "leakage" of ions, water, nutrients, or cells through the vasculature. In some cases, excessive, uncontrolled, or otherwise inappropriate vascular permeability or vascular leakage exacerbates or induces disease states including, e.g., edema associated with tumors including, e.g., brain tumors; ascites associated with malignancies; Meigs' syndrome; lung inflammation; nephrotic syndrome; pericardial effusion; pleural effusion; permeability associated with cardiovascular diseases such as the condition following myocardial infarctions and strokes and the like. The present invention contemplates treating those patients that have developed or are at risk of developing the diseases and disorders associated with abnormal vascular permeability or leakage.

Other patients that are candidates for receiving the antibodies or polypeptides of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

Anti-angiogenesis therapies are useful in the general treatment of graft rejection, lung inflammation, nephrotic syndrome, preeclampsia, pericardial effusion, such as that associated with pericarditis, and pleural effusion, diseases and disorders characterized by undesirable vascular permeability or leakage, e.g., edema associated with tumors including, e.g., brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases according to this invention include angiofibroma (abnormal blood of vessels which are prone to bleeding), neovascular glaucoma (growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

As used herein, "treatment" (and grammatical variations thereof such as "treat" or "treating") refers to administering a compound or a pharmaceutical composition for prophylactic and/or therapeutic purposes. To "treat disease" or use for "therapeutic treatment" refers to administering treatment to a subject already suffering from a disease to improve the subject's condition. Desirable effects of treatment include, but are not limited to, preventing recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease. Preferably, the subject is diagnosed as suffering from a disease having abnormal angiogenesis, based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing a disease having abnormal angiogenesis, using the diagnostic methods described herein.

By "treating or ameliorating" is meant ameliorating a condition or symptoms of the condition before or after its onset. As compared with an equivalent untreated control, such amelioration or degree of treatment is at least 5%, 10%, 20%, 30%, 40%, 50%, 60%, 70%, 80%, 90%, 95%, or 100% as measured by any standard technique.

The terms "recurrence," "relapse" or "relapsed" refers to the return of a cancer or disease after clinical assessment of the disappearance of disease. A diagnosis of distant metastasis or local recurrence can be considered a relapse.

"Refractory" refers to the resistance or non-responsiveness of a disease or condition to a treatment (e.g., the number of neoplastic plasma cells increases even though treatment if given). In certain embodiments, the term "refractory" refers a resistance or non-responsiveness to any previous treatment including, but not limited to, VEGF antagonist, anti-angiogenic agents and chemotherapy treatments. In certain embodiments, the term "refractory" refers an intrinsically non-responsiveness of a disease or condition to any previous treatment comprising a VEGF antagonist, anti-angiogenic agents and/or chemotherapy treatments. In certain embodiments, the VEGF antagonist is an anti-VEGF antibody.

"Relapsed" refers to the regression of the patient's illness back to its former diseased state, especially the return of symptoms following an apparent recovery or partial recovery. In certain embodiments, relapsed state refers to the process of returning to or the return to illness before the previous treatment including, but not limited to, VEGF antagonist, anti-angiogenic agents and/or chemotherapy treatments. In certain embodiments, relapsed state refers to the process of returning to or the return to illness after an initial strong response to a cancer therapy comprising a VEGF antagonist, anti-angiogenic agents and/or chemotherapy treatments. In certain embodiments, the VEGF antagonist is an anti-VEGF antibody.

The term "adjuvant therapy" refers to treatment given after the primary therapy, usually surgery. Adjuvant therapy for cancer or disease may include immune therapy, chemotherapy, radiation therapy or hormone therapy.

The term "maintenance therapy" refers to scheduled retreatment that is given to help maintain a previous treatment's effects. Maintenance therapy is often given to help keep cancer in remission or prolong a response to a specific therapy regardless of disease progression.

The term "invasive cancer" refers to cancer that has spread beyond the layer of tissue in which it started into the normal surrounding tissues. Invasive cancers may or may not be metastatic.

The term "non-invasive cancer" refers to a very early cancer or a cancer that has not spread beyond the tissue of origin.

The term "progression-free survival" in oncology refers to the length of time during and after treatment that a cancer does not grow. Progression-free survival includes the amount of time patients have experienced a complete response or a partial response, as well as the amount of time patients have experienced stable disease.

The term "progressive disease" in oncology can refer to a tumor growth of more than 20 percent since treatment began—either due to an increase in mass or a spread in the tumor.

A "disorder" is any condition that would benefit from treatment with the antibody. For example, mammals who suffer from or need prophylaxis against abnormal angiogenesis (excessive, inappropriate or uncontrolled angiogenesis) or abnormal vascular permeability or leakage. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, head and neck cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), prostate cancer, cancer of the peritoneum, hepatocellular cancer, gastric or stomach cancer including gastrointestinal cancer, pancreatic cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, and Meigs' syndrome.

"Tumor", as used herein, refers to all neoplastic cell growth and proliferation, whether malignant or benign, and all precancerous and cancerous cells and tissues.

The term "anti-neoplastic composition" or "anti-neoplastic agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BAFF, BR3, APRIL, BCMA or VEGF receptor(s), TRAIL/Apo2, and other bioactive and organic chemical agents, etc. Combinations thereof are also contemplated in this invention.

A "growth inhibitory agent" when used herein refers to a compound or composition which inhibits growth or proliferation of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), growth inhibitory agents, chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras and EGFR (e.g., erlotinib (Tarceva™)) that reduce cell proliferation and pharmaceutically acceptable salts, acids or derivatives of any of the above.

Chemotherapeutic agents also include anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance (e.g., small molecule) that is less cytotoxic to diseased cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Isolated," when used to describe the various polypeptides disclosed herein, means polypeptide that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide natural environment will not be present. Ordinarily, however, isolated polypeptide will be prepared by at least one purification step.

An "isolated" polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

The amino acid sequences described herein are contiguous amino acid sequences unless otherwise specified.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand—such as a VEGFR or a fibronectin ligand. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM. Peptibodies, which often comprise a sequence derived from phage display selection of sequences that specifically bind a target fused to an Fc portion of an immunoglobulin, can be considered immunadhesins herein.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one which can specifically bind to VEGF or α5β1. In one embodiment, the antibody can prevent or substantially reduce the ability of a VEGF to induce cell proliferation.

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., BASIC AND CLINICAL IMMUNOLOGY, 8th edition, Daniel P. Stites, Abba I. Ten and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., SEQUENCES OF PROTEINS OF IMMUNOLOGICAL INTEREST, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (in one embodiment, H1 is around about 31-35); Kabat et al., supra and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

Throughout the present specification and claims, the Kabat numbering system is generally used when referring to a residue in the variable domain (approximately, residues 1-107 of the light chain and residues 1-113 of the heavy chain) (e.g, Kabat et al., supra (1991)). The "EU numbering system" or "EU index" is generally used when referring to a residue in an immunoglobulin heavy chain constant region (e.g., the EU index reported in Kabat et al., supra (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al., Nature, 256:495 (1975), or can be made using recombinant DNA methods in bacterial, eukaryotic animal or plant cells (see, e.g., U.S. Pat. No. 4,816,567). The "monoclonal antibodies" can also be isolated from phage antibody libraries using the techniques described in Clackson et al., Nature, 352:624-628 (1991), Marks et al., J. Mol. Biol., 222:581-597 (1991) or using the methods set forth in the Examples below.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., PNAS USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., PNAS USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. For example blocking or antagonist anti-α5β1 antibodies partially or completely inhibit the angiogenesis by binding α5β1.

An "agonist" antibody is one which enhances or increases biological activity of the antigen it binds. For example agonist antibodies anti-α5β1 antibodies enhance angiogenesis by binding α5β1.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

The expression "linear antibodies" generally refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this invention can comprise polypeptides populations with all K447 residues removed, polypeptide populations with no K447 residues removed or polypeptide populations having a mixture of polypeptides with and without the K447 residue.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *PNAS USA*, 90:6444-6448 (1993).

"Humanized" antibodies are forms of non-human (e.g., rodent) antibodies that are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "species-dependent antibody" is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, no more than about $1 \times 10^{-8}$ or no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

In such embodiments, the extent of binding of the polypeptide, antibody, antagonist or composition to a "non-target" protein will be less than about 10% of the binding of the polypeptide, antibody, antagonist or composition to its particular target protein as determined by fluorescence activated cell sorting (FACS) analysis or radioimmunoprecipitation (RIA). With regard to the binding of a polypeptide, antibody, antagonist or composition to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Kabat et al., supra (1991)).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The terms "Fc receptor" or "FcR" are used to describe a receptor that binds to the Fc region of an antibody. In one embodiment, an FcR of this invention is one that binds an IgG antibody (a gamma receptor) and includes includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

WO 00/42072 (Presta) and Shields et al. *J. Biol. Chem.* 9(2): 6591-6604 (2001) describe antibody variants with improved or diminished binding to FcRs. The contents of those publications are specifically incorporated herein by reference.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

An antibody or peptibody with a variant IgG Fc with "altered" FcR binding affinity or ADCC activity is one which has either enhanced or diminished FcR binding activity (e.g, FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3 fold, preferably about 5, 10, 25, 50, 60, 100, 150, 200, 250, 300, 350, 400, 450, or 500 fold, or about 25% to 1000% improvement in binding. The polypeptide variant which "exhibits decreased binding" to an FcR, binds at least one FcR with lower affinity (e.g, higher apparent Kd or higher IC50 value) than a parent polypeptide. The decrease in binding compared to a parent polypeptide may be about 5%, 10%, 20%, 30%, 40%, 50%, 60%, or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using the in vitro ADCC assay as herein disclosed, but other assays or methods for determining ADCC activity, e.g. in an animal model etc, are contemplated. In one embodiment, the preferred variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551 and WO 99/51642. The contents of those patent publications are specifically incorporated herein by reference. See, also, Idusogie et al. *J. Immunol.* 164: 4178-4184 (2000).

"Human effector cells" are leukocytes which express one or more FcRs and perform effector functions. According to one embodiment, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides. In one embodiment, specifically the anti-α5β1 antibodies of the invention having a variant IgG Fc exhibits increased binding affinity for human FcRn over a polypeptide having wild-type IgG Fc, by at least 2 fold, at least 5 fold, at least 10 fold, at least 50 fold, at least 60 fold, at least 70 fold, at least 80 fold, at least 100 fold, at least 125 fold, at least 150 fold. In a specific embodiment, the binding affinity for human FcRn is increased about 170 fold.

For binding affinity to FcRn, in one embodiment, the EC50 or apparent Kd (at pH 6.0) of the polypeptide is less than 1 µM, more preferably less than or equal to 100 nM, more preferably less than or equal to 10 nM. In one embodiment, for increased binding affinity to FcγRIII (F158; i.e. low-affinity isotype) the EC50 or apparent Kd less is than or equal to 10 nM, and for FcγRIII (V158; high-affinity isotype) the EC50 or apparent Kd is less than or equal to 3 nM. According to another embodiment, a reduction in binding of an antibody to a Fc receptor relative to a control antibody (e.g., the Herceptin® antibody) may be considered significant relative to the control antibody if the ratio of the values of the absorbances at the midpoints of the test antibody and control antibody binding curves (e.g, $A_{450\ nm(antibody)}/A_{450\ nm(control\ Ab)}$) is less than or equal to 40%. According to another embodiment, an increase in binding of an antibody to a Fc receptor relative to a control antibody (e.g., the Herceptin® antibody) may be considered significant relative to the control antibody if the ratio of the values of the absorbances at the midpoints of the test antibody and control antibody binding curves (e.g, $A_{450\ nm(antibody)}/A_{450\ nm(control\ Ab)}$) is greater than or equal to 125%.

A "parent polypeptide" or "parent antibody" is a polypeptide or antibody comprising an amino acid sequence from which the variant polypeptide or antibody arose and against which the variant polypeptide or antibody is being compared. Typically the parent polypeptide or parent antibody lacks one or more of the Fc region modifications disclosed herein and differs in effector function compared to a polypeptide variant as herein disclosed. The parent polypeptide may comprise a native sequence Fc region or an Fc region with pre-existing amino acid sequence modifications (such as additions, deletions and/or substitutions).

Antibodies of this invention can be derived from phage display. As used herein, "library" refers to a plurality of antibody or antibody fragment sequences, or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology,* 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

Covalent modifications of polypeptides such as peptibodies, immunoadesins, antibodies and short peptides are included within the scope of this invention. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties,* W.H. Freeman & Co., San Francisco, pp. 79-86 (1983)], acetylation of the N-terminal amine, and amidation of any C-terminal carboxyl group.

Other modifications include the conjugation of toxins to the antagonists such as maytansine and maytansinoids, calicheamicin and other cytotoxic agents.

Another type of covalent modification of the polypeptide comprises linking the polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The polypeptide of the present invention can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an $\alpha$-tubulin epitope peptide [Skinner et al., *J. Biol. Chem.,* 266:15163-15166 (1991)]; and the T7 gene 10 protein peptide tag [Lutz-Freyermuth et al., *PNAS USA,* 87:6393-6397 (1990)].

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this invention include polypeptides that comprise approximately or only residues 94-243, residues 33-53 or residues 33-52 of human in place of at least one variable region within an Ig molecule. In a particularly embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130.

The invention provides methods and compositions for inhibiting or preventing relapse tumor growth or relapse cancer cell growth. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells. A tumor resistant to anti-VEGF treatment is an example of a relapse tumor growth.

An "effective amount" of a polypeptide, antibody, antagonist or composition as disclosed herein is an amount sufficient to carry out a specifically stated purpose. An "effective amount" can be determined empirically and by known methods relating to the stated purpose.

The term "therapeutically effective amount" refers to an amount of an antibody, polypeptide or antagonist of this invention effective to "treat" a disease or disorder in a mammal (aka patient). In the case of cancer, the therapeutically effective amount of the drug can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

In the case of wound healing, the term "effective amount" or "therapeutically effective amount" refers to an amount of a drug effective to accelerate or improve wound healing in a subject. A therapeutic dose is a dose which exhibits a therapeutic effect on the patient and a sub-therapeutic dose is a dose which does not exhibit a therapeutic effect on the patient treated.

A "chronic wound" refers a wound that does not heal. See, e.g., Lazarus et al., Definitions and guidelines for assessment of wounds and evaluation of healing, Arch. Dermatol. 130: 489-93 (1994). Chronic wounds include, but are not limited to, e.g., arterial ulcers, diabetic ulcers, pressure ulcers, venous ulcers, etc. An acute wound can develop into a chronic wound. Acute wounds include, but are not limited to, wounds caused by, e.g., thermal injury, trauma, surgery, excision of extensive skin cancer, deep fungal and bacterial infections, vasculitis, scleroderma, pemphigus, toxic epidermal necrolysis, etc. See, e.g., Buford, Wound Healing and Pressure Sores, HealingWell.com, published on: Oct. 24, 2001. A "normal wound" refers a wound that undergoes normal wound healing repair.

A "growth inhibitory amount" of a polypeptide, antibody, antagonist or composition of this invention is an amount capable of inhibiting the growth of a cell, especially tumor, e.g., cancer cell, either in vitro or in vivo. A "growth inhibitory amount" of a polypeptide, antibody, antagonist or composition of this invention for purposes of inhibiting neoplastic cell growth can be determined empirically and by known methods or by examples provided herein.

A "cytotoxic amount" of a polypeptide, antibody, antagonist or composition of this invention is an amount capable of causing the destruction of a cell, especially tumor, e.g., cancer cell, either in vitro or in vivo. A "cytotoxic amount" of a polypeptide, antibody, antagonist or composition of this invention for purposes of inhibiting neoplastic cell growth can be determined empirically and by methods known in the art.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS, and relapsing remitting MS, progressive systemic sclerosis, atherosclerosis, arteriosclerosis, sclerosis disseminata, and ataxic sclerosis, inflammatory bowel disease (IBD) (for example, Crohn's disease, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN, membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis, cerebellar degeneration, neuromyotonia, opsoclonus or opsoclonus myoclonus syndrome (OMS), and sensory neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune inner ear disease (AIED) or autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "detecting" is intended to include determining the presence or absence of a substance or quantifying the amount of a substance. The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of α5 gene product, a β1 gene product (e.g., mRNA molecules), or an α5 or α5β1 polypeptide; a change in the levels of an α5 or α5β1 polypeptide or amount bound to a target; a change in biological function/activity of an α5 or α5β1 polypeptide. In some embodiments, "detecting" may include detecting wild type α5 or α5β1 levels (e.g., mRNA or polypeptide levels). Detecting may include quantifying a change (e.g., an increase or decrease) of any value of at least about 5%, 10%, 15%, 20%, 25%, 30%, 35%, 40%, 45%, 50%, 55%, 60%, 65%, 70%, 75%, 80%, 85%, 90%, 95%, 100%, or more when compared to a control. Detecting may include quantifying a change of any value of at least about 2-fold, 3-fold, 4-fold, 5-fold, 6-fold, 7-fold, 8-fold, 9-fold, 10-fold, or more e.g., 20-fold, 30-fold, 4-fold, 50-fold, 60-fold, 70-fold, 80-fold, 90-fold, 100-fold or more.

"Label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

III. Anti-α5β1 Antibodies

Antibodies that can bind human α5β1 and competitively inhibit the binding of the anti-α5β1 18C12 antibody to human α5β1 are provided herein. Accordingly, one embodiment of the invention provides antibodies comprising a variable light (VL) sequence set forth in any one of SEQ ID NOS: 2, 3, 4, 5, 6, 7, or 8 and a variable heavy (VH) sequence set forth in any one of SEQ ID NOS: 9, 10, 11, 12, 13, or 14. Human or chimeric (including, e.g., humanized) forms of the antibodies of the anti-α5β1 antibodies described herein are also contemplated.

According to one embodiment, the antibody binds a human α5β1 with a Kd between 500 nM and 1 pM. In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). According to another embodiment, the antibody does not bind αVβ3 or αVβ5 or αVβ1. According to another embodiment, the antibody comprises an Fc sequence of a human IgG, e.g., human IgG1 or human IgG4. In another embodiment, an Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function. For example, WO 00/42072 and Shields et al. *J. Biol. Chem.* 9(2): 6591-6604 (2001) describe antibody variants with improved or diminished binding to FcRs. The contents of those publications are specifically incorporated herein by reference. The antibody can be in the form of a Fab, Fab', a F(ab')₂, single-chain Fv (scFv), an Fv fragment; a diabody and a linear antibody. Also, the antibody can be a multi-specific antibody that binds to α5β1 and is an α5β1 antagonist, but also binds one or more other targets and inhibits their function (e.g., VEGF) or a multi-specific antibody that binds to two or more different sites on α5β1. The antibody can be conjugated to a therapeutic agent (e.g., cytotoxic agent, a radioisotope and a chemotherapeutic agent) or a label for detecting α5β1 in patient samples or in vivo by imaging (e.g., radioisotope, fluorescent dye and enzyme).

Nucleic acid molecules encoding the anti-α5β1 antibodies, expression vectors comprising nucleic acid molecules encoding one or both variable domains, and cells comprising the nucleic acid molecules are also contemplated. These antibodies can be used in the therapies described herein and to detect α5β1 protein in patient samples (e.g., using FACS, immunohistochemistry (IHC), ELISA assays) or in patients.

A. Monoclonal Antibodies

Monoclonal antibodies can be prepared, e.g., using hybridoma methods, such as those described by Kohler and Milstein, *Nature*, 256:495 (1975) or can be made by recombinant DNA methods (U.S. Pat. No. 4,816,567) or can be produced by the methods described herein in the Examples below. In a hybridoma method, a hamster, mouse, or other appropriate host animal is typically immunized with an immunizing agent (e.g., an α5, β1, or α5β1 polypeptide alone or in combination with a suitable carrier) to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, MONOCLONAL ANTIBODIES: PRINCIPLES AND PRACTICE (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al., MONOCLONAL ANTIBODY PRODUCTION TECHNIQUES AND APPLICATIONS (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

B. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 63 (Marcel Dekker, Inc., New York, 1987); and Boerner et al., *J. Immunol.*, 147: 86 (1991).) Human antibodies generated via human B-cell hybridoma technology are also described in Li et al., *PNAS. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

C. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *PNAS USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

D. Chimeric and Humanized Antibodies

In certain embodiments, an antibody provided herein is a chimeric antibody. Certain chimeric antibodies are described, e.g., in U.S. Pat. No. 4,816,567; and Morrison et al., *PNAS USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *PNAS USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer*, 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *PNAS USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

E. Multi-Specific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for α5β1 and the other is for any other antigen (e.g., VEGF). In certain embodiments, bispecific antibodies may bind to two different epitopes of α5β1. Bispecific antibodies may also be used to localize cytotoxic agents to cells which express α5β1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *PNAS USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1). The antibody or fragment herein also includes a "Dual Acting FAb" or "DAF" comprising an antigen binding site that binds to α5β1 as well as another, different antigen (see, US 2008/0069820, for example).

F. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Tip, Tyr, Phe.
Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

2. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

3. Fc Region Variants

In certain embodiments, one or more amino acid modifications may be introduced into the Fc region of an antibody provided herein, thereby generating an Fc region variant, so as to enhance, e.g., the effectiveness of the antibody in treating a disease or disorder involving abnormal angiogenesis and/or vascular permeability or leakage. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *PNAS USA* 83:7059-7063 (1986)) and Hellstrom, I et al., *PNAS USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737, 056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Mutations or alterations in the Fc region sequences can be made to improve FcR binding (e.g., FcgammaR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields, R L et al. (2001) *JBC* 276(6)6591-6604; Presta, L. G., (2002) *Biochemical Society Transactions* 30(4):487-490; and WO 00/42072. Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

4. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In some embodiments, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.*, 176: 1191-1195 (1992) and Shopes, *J. Immunol.*, 148: 2918-2922 (1992). Homodimeric antibodies with enhanced anti-tumor activity can also be prepared using heterobifunctional cross-linkers as described in Wolff et al., *Cancer Research,* 53: 2560-2565 (1993). Alternatively, an antibody can be engineered that has dual Fc regions and can thereby have enhanced complement lysis and ADCC capabilities. See, Stevenson et al., *Anti-Cancer Drug Design,* 3: 219-230 (1989).

5. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

G. Immunoconjugates

The invention also provides immunoconjugates comprising an anti-α5β1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem.*

Letters 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

H. Immunoliposomes

The antibodies disclosed herein can also be formulated as immunoliposomes. Liposomes containing the antibody are prepared by methods known in the art, such as described in Epstein et al., *PNAS USA,* 82: 3688 (1985); Hwang et al., *PNAS USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. An antineoplastic agent, a growth inhibitory agent, or a chemotherapeutic agent (such as Doxorubicin) is optionally also contained within the liposome. See, Gabizon et al., *J. National Cancer Inst.,* 81(19): 1484 (1989).

IV. Therapeutic Methods Using Anti-α5β1 Antibodies

Any of the anti-α5β1 antibodies provided herein may be used in therapeutic methods. It is understood that any of the formulations or therapeutic methods described herein may be use an immunoconjugate of the invention in place of or in addition to an anti-α5β1 antibody.

In one aspect, an anti-α5β1 antibody for use as a medicament is provided. In further aspects, an anti-α5β1 antibody for use in treating diseases and disorders involving abnormal angiogenesis and/or vascular permeability or leakage, including, for example, cancer, ocular diseases, and immune disorders (e.g., autoimmune disorders) is provided. In certain embodiments, an anti-α5β1 antibody for use in a method of treatment is provided. In certain embodiments, the invention provides an anti-α5β1 antibody for use in a method of treating an individual having a disease or disorder involving abnormal angiogenesis and/or vascular permeability or leakage comprising administering to the individual an effective amount of the anti-α5β1 antibody. In one such embodiment, the method further comprises administering to the individual an effective amount of at least one, two, three, four, or more additional therapeutic agent(s), including, e.g., an antiangiogenic agent, an anti-neoplastic agent, a growth inhibitory agent, or a chemotherapeutic agent as described herein. In further embodiments, the invention provides an anti-α5β1 antibody for use in inhibiting abnormal angiogenesis and/or vascular permeability or leakage. In certain embodiments, the invention provides an anti-α5β1 antibody for use in a method of inhibiting abnormal angiogenesis and/or vascular permeability or leakage in an individual comprising administering to the individual an effective of the anti-α5β1 antibody to inhibit abnormal angiogenesis and/or vascular permeability or leakage. An "individual" according to any of the above embodiments is preferably a human.

In a further aspect, the invention provides for the use of an anti-α5β1 antibody in the manufacture or preparation of a medicament. In one embodiment, the medicament is for treatment of a disease or disorder involving abnormal angiogenesis and/or vascular permeability or leakage In a further embodiment, the medicament is for use in a method of treating a disease or disorder involving abnormal angiogenesis and/or vascular permeability or leakage comprising administering to an individual having a disease or disorder involving abnormal angiogenesis and/or vascular permeability or leakage an effective amount of the medicament. In one such embodiment, the method further comprises administering to the individual an effective amount of at least one, two, three, four, or more additional therapeutic agent(s) including, e.g., an antiangiogenic agent, an anti-neoplastic agent, a growth inhibitory agent, or a chemotherapeutic agent as described herein. In a further embodiment, the medicament is for inhibiting abnormal angiogenesis and/or vascular permeability or leakage. In a further embodiment, the medicament is for use in a method of inhibiting abnormal angiogenesis and/or vascular permeability or leakage in an individual comprising administering to the individual an amount effective of the medicament to inhibit abnormal angiogenesis and/or vascular permeability or leakage. An "individual" according to any of the above embodiments may be a human.

In a further aspect, the invention provides a method for treating a disease or disorder involving abnormal angiogenesis and/or vascular permeability or leakage. In one embodiment, the method comprises administering to an individual having such a disease or disorder involving abnormal angiogenesis and/or vascular permeability or leakage an effective amount of an anti-α5β1 antibody. In one such embodiment, the method further comprises administering to the individual an effective amount of at least one additional therapeutic agent, as described below. An "individual" according to any of the above embodiments may be a human.

In a further aspect, the invention provides a method for inhibiting abnormal angiogenesis and/or vascular permeability or leakage in an individual. In one embodiment, the method comprises administering to the individual an effective amount of an anti-α5β1 antibody to inhibit abnormal angiogenesis and/or vascular permeability or leakage. In one embodiment, an "individual" is a human.

In a further aspect, the invention provides pharmaceutical formulations comprising any of the anti-α5β1 antibodies provided herein, e.g., for use in any of the above therapeutic methods. In one embodiment, a pharmaceutical formulation comprises any of the anti-α5β1 antibodies provided herein and a pharmaceutically acceptable carrier. In another embodiment, a pharmaceutical formulation comprises any of the anti-α5β1 antibodies provided herein and at least one additional therapeutic agent, e.g., as described herein.

Combination therapies described herein encompass combined administration (where two, three, four, or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

In certain embodiments, an additional therapeutic agent is a VEGF antagonist (e.g., an anti-VEGF antibody such as, for example, bevacizumab). In some embodiments, the anti-α5β1 antibodies are administered in combination with a VEGF antagonist. The anti-α5β1 antibody and additional agent (e.g., a VEGF antagonist) can be administered concurrently or sequentially. Alternatively, the subject can be treated with the VEGF antagonist and subsequently administered the α5β1 antagonist, e.g., treating with the VEGF antagonist until the subject is unresponsive to VEGF antagonist treatment and then treating the subject is treated with an α5β1 antagonist. According to one embodiment, the subject is treated with the VEGF antagonist when the cancer is non-invasive and then treated with the α5β1 antagonist when the cancer is invasive. Some patients who experience elevated α5β1 levels naturally or in response to VEGF antagonist therapy, compared to non-diseased patients or control, can be especially responsive to this combination treatment. Combinations further comprising a therapeutic agent (e.g., an anti-neoplastic agent, a chemotherapeutic agent, a growth inhibitory agent and a cytotoxic agent) are contemplated. For example, patients who are to be treated with chemotherapy (e.g., irinotecan) and α5β1 antagonists, or who have been treated with chemotherapy and α5β1 antagonists, can benefit from VEGF antagonist therapy. Alternatively, patients who have been treated with chemotherapy and VEGF antagonists can benefit from α5β1 antagonist therapy. In one embodiment, the anti-VEGF antibody is bevacizumab. In another embodiment, the anti-α5β1 antibody is an anti-α5β1 antibody described herein.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Depending on the indication to be treated and factors relevant to the dosing that a physician of skill in the field would be familiar with, the antibodies of the invention will be administered at a dosage that is efficacious for the treatment of that indication while minimizing toxicity and side effects.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Because the anti-angiogenic agents described herein target the tumor vasculature and not necessarily the neoplastic cells themselves, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the $\alpha 5\beta 1$ antagonists and VEGF antagonists of the invention may cause inhibition of metastatic spread without shrinkage of the primary tumor, or may simply exert a tumouristatic effect. Accordingly, approaches to determining efficacy of the therapy can be employed, including for example, measurement of plasma or urinary markers of angiogenesis and measurement of response through radiological imaging.

Evaluation of treatments for age-related macular degeneration (AMD) includes, but it is not limited to, a decrease in the rate of further vision loss or the prevention of further vision loss. For AMD therapy, efficacy in vivo can, for example, be measured by one or more of the following: assessing the mean change in the best corrected visual acuity (BCVA) from baseline to a desired time, assessing the proportion of subjects who lose fewer than 15 letters in visual acuity at a desired time compared with baseline, assessing the proportion of subjects who gain greater than or equal to 15 letters in visual acuity at a desired time compared with baseline, assessing the proportion of subjects with a visual-acuity Snellen equivalent of 20/2000 or worse at desired time, assessing the NEI Visual Functioning Questionnaire, assessing the size of CNV and amount of leakage of CNV at a desired time, as assessed by fluorescein angiography, and the like.

V. Pharmaceutical Formulations

The anti-$\alpha 5\beta 1$ antibodies can be formulated with suitable carriers or excipients so that they are suitable for administration. Suitable formulations of the antibodies are obtained by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations are described in WO98/56418, expressly incorporated herein by reference. Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, and/or a chemotherapeutic agent. Such molecules are suitably present in combination in amounts that are effective for the purpose intended. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Lipofectins or liposomes can be used to deliver the polypeptides and antibodies or compositions of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., PNAS USA, 90: 7889-7893 (1993).

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The formulations to be used for in vivo administration must be sterile. This is readily accomplished by filtration through sterile filtration membranes.

VI. Methods of Diagnosis and Imaging Using Anti-α5β1 Antibodies

Labeled anti-α5β1 antibodies, and derivatives and analogs thereof, which specifically bind to an α5β1 polypeptide can be used for diagnostic purposes to detect, diagnose, or monitor diseases and/or disorders associated with the expression, aberrant expression and/or activity of α5β1. For example, the anti-α5β1 antibodies of the invention can be used in in situ, in vivo, ex vivo, and in vitro diagnostic assays or imaging assays.

Methods for detecting expression of an α5β1 polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression.

Additional embodiments of the invention include methods of diagnosing a disease or disorder associated with expression or aberrant expression of α5β1 in an animal (e.g., a mammal such as a human). The methods comprise detecting α5β1 molecules in the mammal. In one embodiment, after administering a VEGF antagonist, diagnosis comprises: (a) administering an effective amount of a labeled anti-α5β1 antibody to a mammal (b) waiting for a time interval following the administering for permitting the labeled α5β1 antibody to preferentially concentrate at sites in the subject where the α5β1 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of α5β1. Background level can be determined by various methods including, comparing the amount of labeled molecule detected to a standard value previously determined for a particular system.

Anti-α5β1 antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

According to one specific embodiment, α5β1 polypeptide expression or overexpression is determined in a diagnostic or prognostic assay after administration of a VEGF antagonist therapeutic agent by evaluating levels of α5β1 present on the surface of a cell (e.g., via an immunohistochemistry assay using anti-α5β1 antibodies). Alternatively, or additionally, one can measure levels of α5β1 polypeptide-encoding nucleic acid or mRNA in the cell, e.g., via fluorescent in situ hybridization using a nucleic acid based probe corresponding to an α5β1-encoding nucleic acid or the complement thereof; (FISH; see WO98/45479 published October, 1998), Southern blotting, Northern blotting, or polymerase chain reaction (PCR) techniques, such as real time quantitative PCR(RT-PCR). One can also study α5β1 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the can be evaluated, e.g., by external scanning for radioactivity or by analyzing a sample (e.g., a biopsy or other biological sample) taken from a mammal previously exposed to the antibody.

VII. Articles of Manufacture and Kits

Another embodiment of the invention is an article of manufacture containing materials useful for the treatment of cancer (e.g. tumors), ocular disease (e.g., wet AMD) or autoimmune diseases and related conditions. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is a VEGF antagonist or an α5β1 antagonist or an VEGF agonist or an α5β1 agonist of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products, that contain information about the indications, usage, dosage, administration, contraindications and/or warnings concerning the use of such therapeutic products.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of α5β1 and/or VEGF in patients, optionally in combination with the articles of manufacture. For isolation and purification of α5β1, the kit can contain an anti-α5β1 antibody coupled to beads (e.g., sepharose beads). Kits can be provided which contain the antibodies for detection and quantitation of α5β1 and/or VEGF in vitro, e.g. in an ELISA or a Western blot. As with the article of manufacture, the kit comprises a container and a label or package insert on or associated with the container. For example, the container holds a composition comprising at least one anti-α5β1 antibody of the invention. Additional containers may be included that contain, e.g., diluents and buffers, control antibodies. The label or package insert may provide a description of the composition as well as instructions for the intended in vitro or diagnostic use.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., CURRENT PROTOCOLS IN MOLECULAR BIOLOGY (Green Publishing Associates and Wiley Interscience, N.Y., 1989); Innis et al., PCR PROTOCOLS: A GUIDE TO METHODS AND APPLICATIONS (Academic Press, Inc.: N.Y., 1990); Harlow et al., ANTIBODIES: A LABORATORY MANUAL (Cold Spring Harbor Press: Cold Spring Harbor, 1988); Gait, OLIGONUCLEOTIDE SYNTHESIS (IRL Press: Oxford, 1984); Freshney, ANIMAL CELL CULTURE, 1987; Coligan et al., CURRENT PROTOCOLS IN IMMUNOLOGY, 1991.

EXAMPLES

The following examples are offered to illustrate, but not to limit the claimed invention. Those of skill in the art will readily recognize a variety of noncritical parameters which can be changed or modified to yield essentially the same results.

Example 1

Materials and Methods

A. BIAcore Analysis:

To determine binding kinetics and affinities of the antibodies described herein, Surface Plasmon Resonance (SRP) measurement with a BIAcore™-3000 instrument was used. Antibody was first captured by pre-immobilized rabbit anti-human Fc CM5 biosensor chip on the different flow cell to achieve approximately 150 RU (Response Units). For kinetics measurements, 2-fold serial dilutions of human integrin α5β1 (300 nM to 1.2 nM) were injected in PBT buffer (PBS with 0.05% Tween 20) at 25° C. with a flow rate of 300 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

B. Fibronectin Binding Assay with U937 Cells

100 μl of 10 μg/ml Fibronectin (R & D Systems) diluted in PBS pH 7.4 was added to the wells of 96-well plates (Nucn MaxiSorp) and incubated overnight at 2-8° C. Plates were washed 3 times with 200 μl PBS pH 7.4. 200 μl PBS pH 7.4/1% BSA was added to all wells and the plates were incubated for at least 60 minutes at room temperature with gentle agitation. Plates were washed 3 times with 200 μl PBS pH 7.4.

50 μl of diluted anti-α5β1 antibody was added to each well (10 μg/mL serially diluted 1:3 10 times), immediately followed by 50 μl U937 cells (ATCC, Cat#CRL-1593.2) at a concentration of 1×10$^6$ cells/mL in Assay Media (RPMI 1640 (Media Prep A0806), 5 mg/mL BSA, 1 mM L-glutamine, 1 mM MgCl$_2$).

Plates were incubated for 30 min at 37° C., unbound cells were discarded and the plates were washed with twice with 150 μL Assay Media. 100 μl of Assay Media and 100 μl of Cell-Titer Glow (Promega Cat#G7573) were added to each well. The plates were incubated for 10-15 minutes at room temperature, covered. Luminescence was detected on a VICTOR $^2$V (Perkin-Elmer) plate reader and the luminescence units were analyzed relative to the concentration of the antibodies used in the assay, using a four-parameter nonlinear least squares fit, to obtain the IC$_{50}$ values.

C. Fibronectin Binding Assay with α5β1

25 μl of 1 μg/ml Fibronectin (R & D Systems) diluted in PBS, was added to the wells of 384-well plates (Nucn MaxiSorp) and incubated overnight at 2-8° C. Plates were washed 3 times with 80 μL PBT buffer. 50 μl PBS/1% BSA was added to all wells, the plates were incubated for at least 60 minutes at room temperature with gentle agitation, then washed 3 times with 80 μL PBT buffer.

anti-α5β1 antibody (30 μg/mL) was serially diluted 1:3 11 times. 50 μl of the serially diluted anti-α5β1 antibody was added to 0.65 mL micro tubes and premixed (1:1) with 50 μL of 200 ng/mL α5β1 (R & D Systems) in ELISA buffer (150 mM NaCl, 10 mM Tris, pH 7.5, 5 mg/mL BSA, 1 mM $MnCl_2$) for 60 minutes at room temperature with gentle agitation. 25 μL of the premixed α5β1 and anti-α5β1 antibody was added to the Fibronectin coated wells and the plates were incubated at room temperature for 60 minutes with gentle agitation. Plates were washed 6 times with PBT buffer, 100 ng/mL anti-β1-biotin in ELISA buffer was added to each well and the plates were incubated for 60 minutes at room temperature with gentle agitation. Plates were washed 6 times with 80 μL PBT buffer, 25 μL of Streptadvidin-HRP (1:50,000 in ELISA buffer, GE Healthcare) was added to each well, and the plates were incubated for 60 minutes at room temperature with gentle agitation. Plates were washed 6 times with 80 μL PBT buffer, 25 μL of TMB substrate (Kirkgaard and Perry Laboratories) was added to each well, plates were incubated about 6 minutes at room temperature, and the reaction was stopped with 25 μL of 1 M Phosphoric Acid. Absorbance was read at 450 nm and $IC_{50}$ values were analyzed as described in section B above.

D. HUVEC Migration Assay

HUVEC cells were grown in standard media to 80% confluency. The cells were trypsinized, counted, and resuspended in EBM-2 media with 0.1% BSA at a concentration of $5 \times 10^5$ cells/ml. For the assay, 100 μl of cells ($5 \times 10^4$ cells/well) were plated per well in a BD Falcon HTS Multiwell System 24 well (BD Ref: 351185, Pore size 8 μm). The HTS plates were pre-coated with Fibronectin (1-2 μg/ml) overnight. The plates were washed with PBS and 500 μl (EBM with 0.1% BSA) solution was added to the bottom chamber. For each sample, 3-6 wells were used. No migration stimulus (e.g., VEGF) was added to the negative control well.

To start the assay, 100 μl of cells ($5 \times 10^4$ cells/well) were added to the upper chamber. The lower chamber contained 500 μl of media (EBM with 0.1% BSA). Anti-integrin α5β1 antibodies and isotype controls are generally added to the upper chamber with the cells at a final concentration of 0 μg/ml, 1 μg/ml or 5 μg/ml, and incubated for 15 minutes before the migration stimulus (VEGF) was added to the lower chamber.

Stimulus was added to the lower chamber (10 ng/ml VEGF-A), and plates were incubated 4-6 hours, or overnight. Cells were scraped from the upper chamber using a sponge swab, PBS was added, then the cells from the upper chamber were scraped again. The media was drained from the lower chamber and the cells were fixed with 500 μl of 100% methanol for 5 minutes.

The cells were then stained with 500 μl SYTOX® Green nuclei acid stain (1:5000 or 1:10000 dilution in PBS) (Molecular Probes S7020) for at least 10 min (in the dark). Then, a microscope was used to take individual pictures of each well. Pictures were taking using an AxioVision AC program and a 5× objective.

ImageJ was used to analyze the results (minimum 5 pixels, bin 5). The number of cells per well was recorded and analyzed using Microsoft Excel.

Example 2

Generation of Anti-α5β1 Antibodies

Figure 1B:
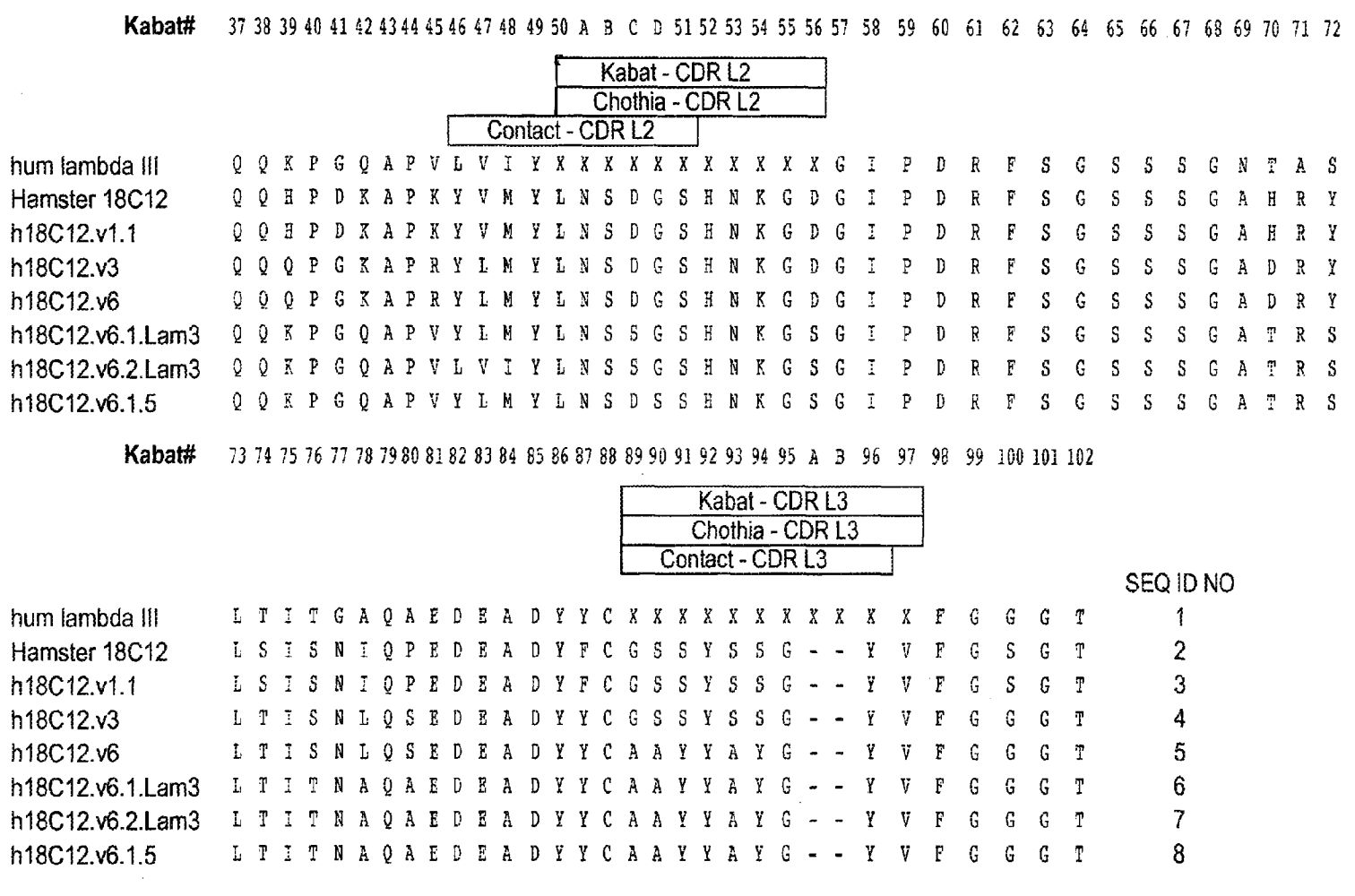

Anti α5β1 antibodies were generated by immunizing hamsters with recombinant human α5β1 extracellular domain polypeptides. Hamster monoclonal antibody clone 18C12 comprising the VH and VL sequences set forth in FIGS. 1 and 2 was selected.

Two versions of chimeric hamster 18C12, h18C12.v1.1 and h18C12.v2.1, were generated by cloning the light chain from the hamster 18C12 into two consensus $VL_{kappa1}/VH_{III}$ frameworks: h18C12.v1.1 and h18C12.v2.1 which differ only in the CDR-H3 contact region. Specifically, the CDR-H3 contact region of h18C12.v1.1 comprises the following residues: $C^{92}A^{93}R^{94}$ and the CDR-H3 contact region of h18C12.v2.1 comprises the following residues: $C^{92}T^{93}S^{94}$. Both h18C12.v1.1 and h18C12.v2.1 were successfully displayed on phage in Fab format and binding was observed by phage competition ELISA. No significant differences in binding were observed between h18C12.v1.1 and h18C12.v2.1. h18C12.v1.1 was selected for further humanization. Humanized 18C12.v3 was generated by changing most of the light chain framework of h18C12.v1.1 into the human consensus lambda IV framework with the exception of the following residues in the light chain: Y36, A43, and Y49. In addition, the following residues in the human $VH_{III}$ framework: G49 and D73 were retained.

h18C12.v3 was affinity matured and the following clones were generated: h18C12.v6; h18C12.v7; h18C12.v9; h18C12.v15; h18C12.v16; h18C12.v28; h18C12.v30; h18C12.v51; h18C12.v54; h18C12.v70; h18C12.v78. CDR sequences for each of the clones are set forth in FIG. 3. CDR sequences for the h18C12.v6 clone were modified as follows: CDR-L2: D50cS and D56S; CDR-H1: N31A; and CDR-H2: N53A. The modified CDR sequences were then inserted into a modified human λIII/VHIII framework to generate h18C12.v6.1Lam3 (h18C12.v6.1) and h18C12.v6.2Lam3 (h18C12.v6.2). The modified human λIII framework for h18C12.v6.1 contained the following modifications: L46Y; V47L; I48M; N69A; A71R; and G77N. The modified human λIII framework for h18C12.v6.2 contained the following modifications: N69A; A71R; and G77N. The modified VHIII framework contained the following modifications: S49G and N73D.

Clone h18C12.v6.1 was further modified to remove Asparagine (N) in CDR-L2 ($N^{50a}S^{50b}S^{50c}G^{50d}$). The following clones were generated: h18C12.v6.1.1; h18C12.v6.1.2; h18C12.v6.1.3; h18C12.v6.1.4; and h18C12.v6.1.5. The CDR-L2 sequence at positions 50a, 50b, 50c, and 50d for each of the h18C12.v6.1 clones is set forth in FIG. 7.

Example 3

Phage Competition ELISA

MAXISORP™ microtiter plates were coated with recombinant human integrin α5β1 (R&D) at 5 μg/ml in PBS overnight and then blocked with PBST buffer (0.5% BSA and 0.05% Tween 20 in PBS) for an hour at room temperature. Phage from culture supernatants were incubated with serially diluted human integrin α5β1 in PBST buffer in a tissue-culture microtiter plate for an hour, after which 80 μl of the mixture was transferred to the target-coated wells for 15 minutes to capture unbound phage. The plate was washed with PBT buffer (0.05% Tween 20 in PBS), and HRP-conjugated anti-M13 (Amersham Pharmacia Biotech) was added (1:5000 in PBST buffer) for 40 minutes. The plate was washed with PBT buffer and developed by adding tetramethylbenzidine substrate (Kirkegaard and Perry Laboratories, Gaithersburg, Md.). The absorbance at 450 nm was plotted as a function of target concentration in solution to determine phage $IC_{50}$. This was used as an affinity estimate for the Fab clone displayed on the surface of the phage. FIG. 4 depicts results from a phage competition assay demonstrating the binding of the affinity matured 18C12 variants h18C12.v3;

h18C12.v6; h18C12.v7; h18C12.v9; h18C12.v15; h18C12.v16; h18C12.v28; h18C12.v30; h18C12.v51; h18C12.v54; h18C12.v70; and h18C12.v78 to human α5β1 integrin.

Example 4

Antibody Affinity Determinations by BIACore

To determine binding kinetics and affinities of chimeric 18C12, h18C12.v6.1, h18C12.v6.1.1, h18C12.v6.1.2, h18C12.v6.1.3, h18C12.v6.1.4, h18C12.v6.1.5 IgGs, Surface Plasmon Resonance (SRP) measurement with a BIAcore™-3000 instrument as described in Example 1 was used.

FIG. 5 depicts results from BIAcore analysis of the binding of affinity matured 18C12 variants to human α5β1 integrin. FIG. 6 depicts results from BIACore analysis of the binding of chimeric 18C12 (18C12 comprising the hamster VL and VH sequences set forth in FIG. 1 and the Fc portion of IgG1) and h18C12.v6.1 to human α5β1 integrin. The data demonstrate that h18C12.v6.1 has a binding affinity for human α5β1 integrin that is approximately 2 times higher than the binding affinity of hamster 18C12 for human α5β1 integrin. FIG. 7 depicts results from BIAcore analysis for each of the h18C12.v6.1 clones.

Example 5

18C12 Antibodies Inhibit Binding to Fibronectin

To compare the effects of chimeric 18C12 and h18C12.v6.1 or h18C12.v6.1.5 IgGs on binding to fibronectin, the fibronectin binding assays described in Example 1 above was used.

Figure 8:
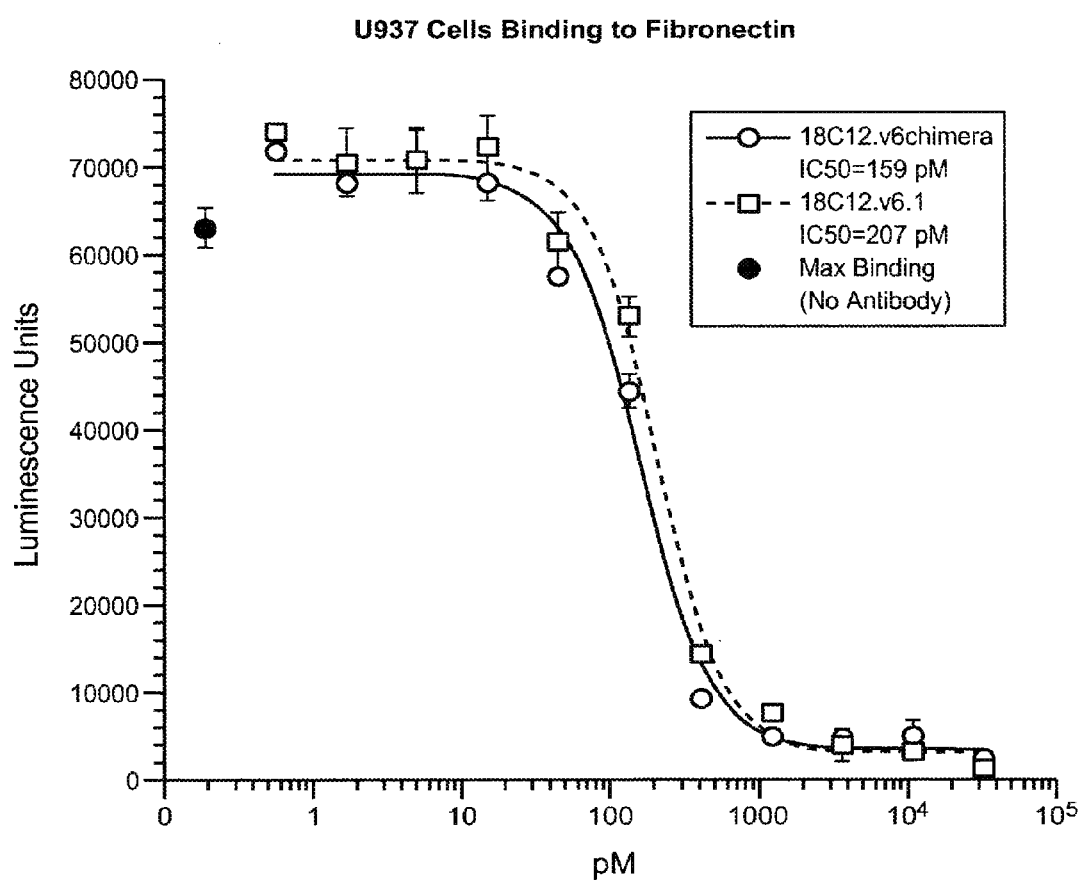
FIG. 8 depicts the results of a fibronectin binding assay comparing the ability of chimeric 18C12 and h18C12.v6.1 to interfere with the binding of U937 cells to fibronectin.
Figure 9:
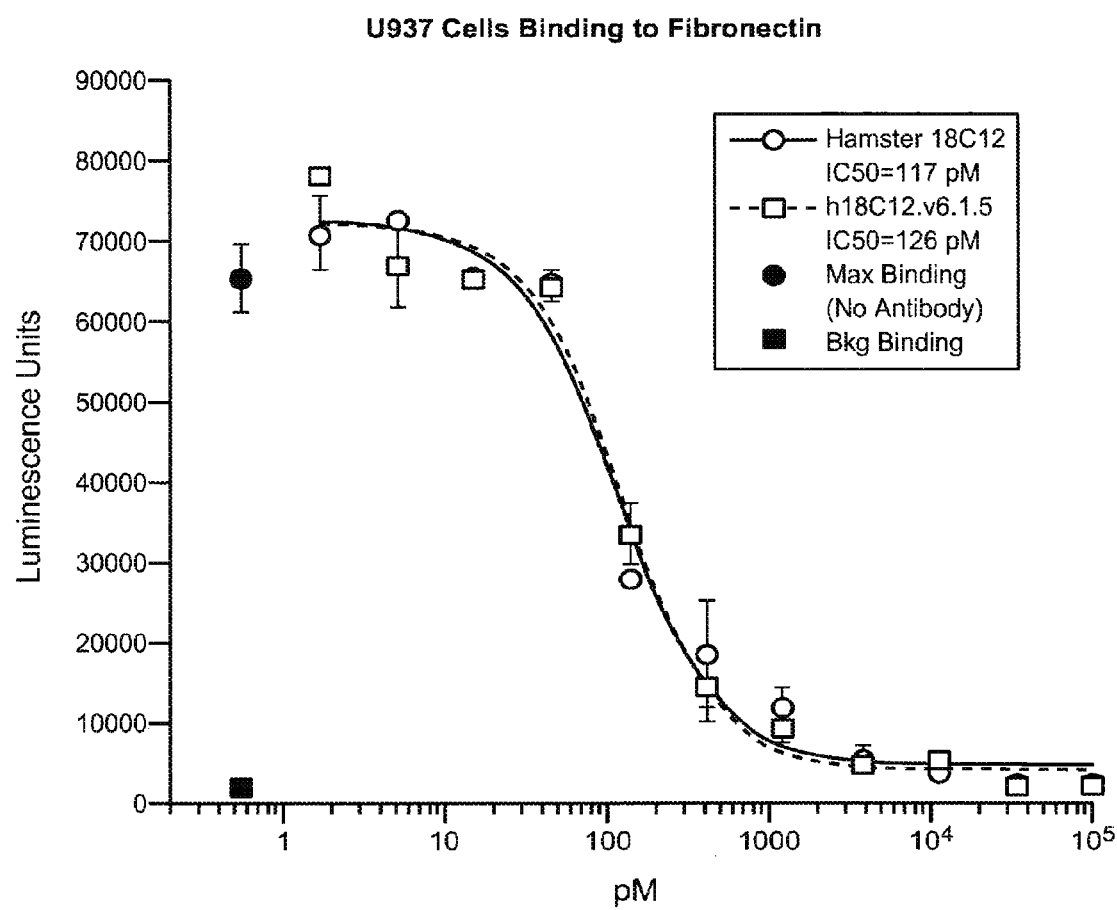
FIG. 9 depicts the results of a fibronectin binding assay comparing the ability of hamster 18C12 and h18C12.v6.1.5 to interfere with the binding of U937 cells to fibronectin.
Figure 10:
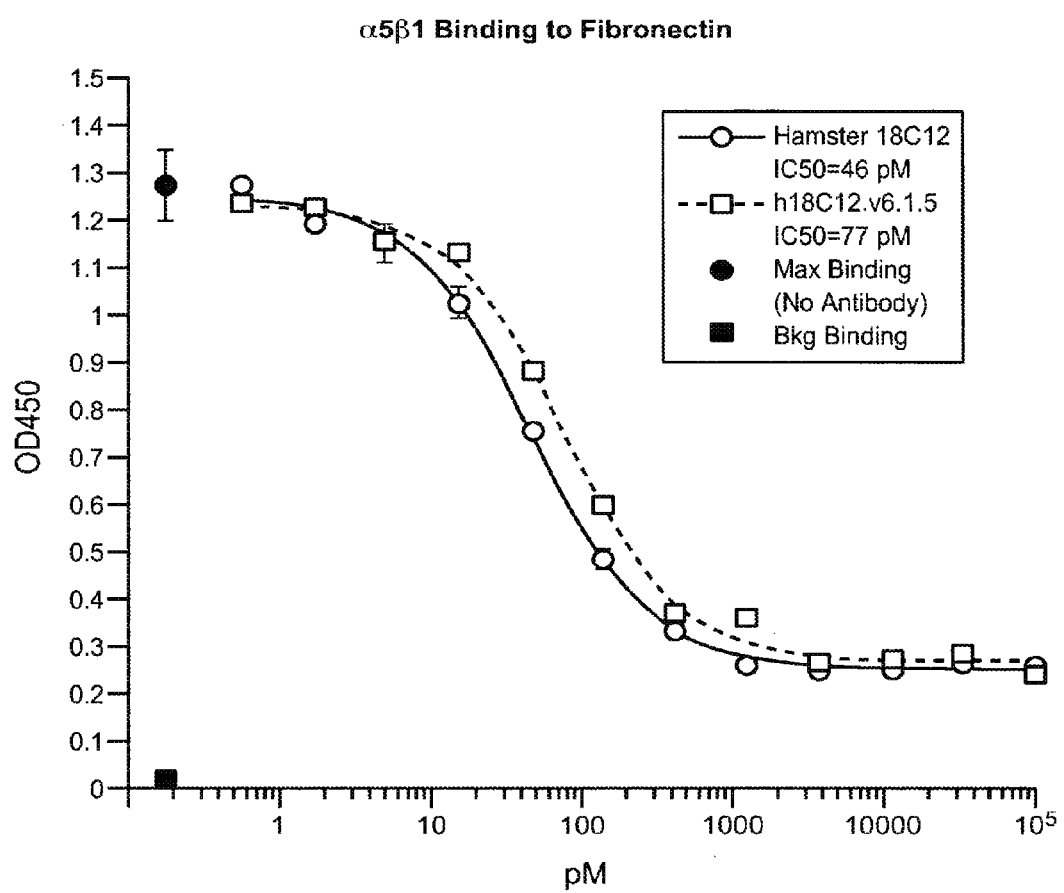
FIG. 10 depicts the results of a fibronectin binding assay comparing the ability of hamster 18C12 and h18C12.v6.1.5 to interfere with the binding of $\alpha_5\beta_1$ to fibronectin.

FIG. 8 depicts the results of a fibronectin binding assay comparing the ability of chimeric 18C12 and h18C12.v6.1 to interfere with the binding of U937 cells to fibronectin. FIG. 9 depicts the results of a fibronectin binding assay comparing the ability of hamster 18C12 and h18C12.v6.1.5 to interfere with the binding of U937 cells to fibronectin. FIG. 10 depicts the results of a fibronectin binding assay comparing the ability of hamster 18C12 and h18C12.v6.1.5 to interfere with the binding of recombinant $\alpha_5\beta_1$ extracellular domain to fibrinectin. The data demonstrate that hamster 18C12, chimeric 18C12, h18C12.v6.1, and h18C12.v6.1.5 inhibit binding of U937 cells or recombinant $\alpha_5\beta_1$ extracellular domain to fibrinectin.

Example 6

18C12 Antibodies Inhibit HUVEC Migration

To compare the effects of chimeric 18C12 and h18C12.v6.1 IgGs on migration of HUVEC cells, the HUVEC migration assay described in Example 1 above was used.

Figure 11:
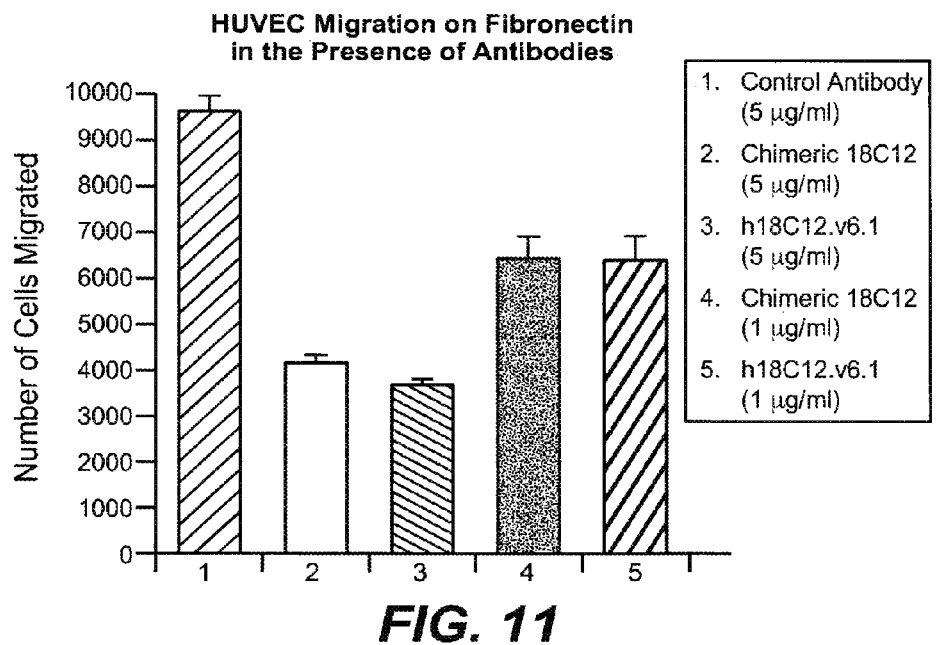
FIG. 11 depicts the results of a HUVEC migration assay comparing the ability of chimeric 18C12 and h18C12.v6.1 to interfere with migration of HUVEC cells on fibronectin.

FIG. 11 depicts the results of a HUVEC migration assay comparing the ability of chimeric 18C12 and h18C12.v6.1 to interfere with migration of HUVEC cells on fibronectin. The data demonstrate that chimeric 18C12 and h18C12.v6.1 inhibit migration of HUVEC cells on fibrinectin.

Example 7

Embryonic Development Assays

α5 transgenic mice expressing a chimeric α5β1 integrin (human α5 and murine β1) were used in embryonic development assays to demonstrate the efficacy of the 18C12 antibodies described herein. Male transgenic mice expressing human α5 and no murine α5 were mated to female mice not expressing human α5 and heterozygous for murine α5. Pregnant mice were injected i.p. with 10 mg/kg anti-α5β1 antibody (h18C12.v6.1.5) or with a negative control antibody 2×/week starting at 9.5 days post-coitum. At day 14.5 post-coitum, the embryos were collected, genotyped, and embryonic vasculature was evaluated. The results are summarized in the table below.

| Treatment | Integrin α5 Expression | Vascular Development |
|---|---|---|
| h18C12.v6.1.5 | only human α5 | Hemorrhage, stunting, and extensive systemic edema |
| h18C12.v6.1.5 | only murine α5 | Normal |
| negative control antibody | only human α5 | Normal |
| negative control antibody | only murine α5 | Normal |

These results demonstrate that h18C12.v6.1.5 disrupts α5β1 integrin function in vivo during vascular development.

Example 8

Tumor Allograft Assays

C57/B16 allograft tumor models are used in studies to demonstrate the efficacy of the 18C12 antibodies described herein. C57/B16 tumor cells are implanted into murine α5 knockout::human α5 transgenic mice and the mice are treated with anti-α5β1 antibodies.

Mice bearing established tumors are randomized into four groups, so that all the groups have similar starting tumor volumes. The dosing regimen is as follows:
  (1) Negative control antibody (13.5 mg/kg, 2×/week)
  (2) Anti-VEGF antibody (3.5 mg/kg, 2×/week)+Negative control antibody (10 mg/kg, 2×/week)
  (3) Negative control antibody (3.5 mg/kg, 2×/week)+anti-α5β1 antibody (18C12) (10 mg/kg, 2×/week)
  (4) Anti-VEGF antibody (3.5 mg/kg, 2×/week)+anti-α5β1 antibody (18C12) (10 mg/kg, 2×/week)

The length and width of tumors are measured twice per week using calipers, and tumor volumes calculated using this formulus: Tumor Volume (mm$^3$)=(w$^2$×l)/2, where w=width and l=length in mm. Tumor volumes are plotted against time to reflect tumor growth rates.

Example 9

Tumor Xenograft Assays

Tumor xenograft assays were used in studies to demonstrate the efficacy of the 18C12 antibodies described herein. Human U87 glioma cells harbouring a luciferase reporter gene are implanted into the brains of nude mice and the mice are treated with anti-α5β1 antibodies.

Mice bearing established tumors were imaged using bioluminescence imaging and randomized into three groups, so that all the groups had a similar starting tumor burden. The dosing regimen was as follows:
  (1) Negative control antibodies (ragweed) (5 mg/kg, 2×/week)+anti-gD (10 mg/kg, 2×/week)
  (2) Anti-VEGF antibody (B20-4.1) (5 mg/kg, 2×/week)+ negative control antibody anti-gD (10 mg/kg, 2×/week)
  (3) Anti-VEGF antibody (B20-4.1) (5 mg/kg, 2×/week)+ anti-α5β1 antibody (h18C12.v6.1.5) (10 mg/kg, 2×/week)

Figure 12:
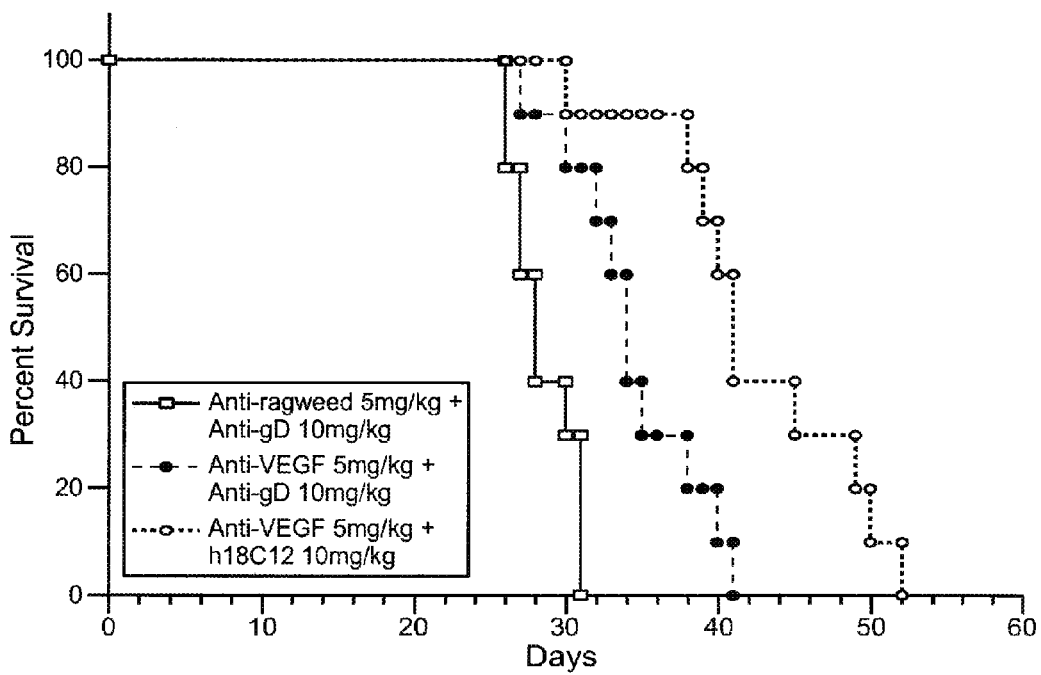
FIG. 12 depicts the results of a tumor xenograft assay measuring the ability of h18C12.v6.1.5+/− anti-VEGF to enhance survival.
Figure 13:
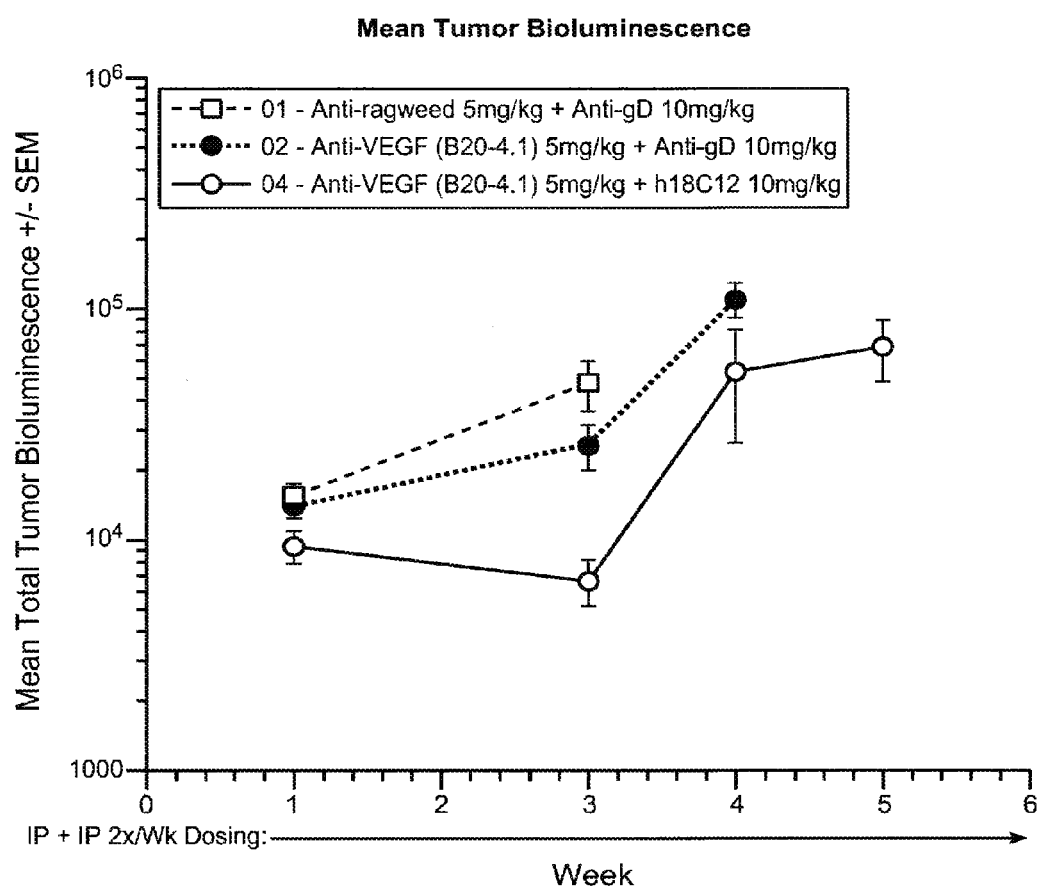
FIG. 13 depicts the results of a tumor xenograft assay measuring the ability of h18C12.v6.1.5+/− anti-VEGF to reduce tumor burden.

The survival of these mice was monitored daily following surgical implantation of tumor cells. Treatment with the anti-α5β1 antibody h18C12.v6.1.5 in combination with anti-VEGF significantly enhanced the survival of mice relative to anti-VEGF alone. The results are shown in FIG. 12. Tumor burdens were also measured at weeks 1, 3, 4, and 5 following implantation using bioluminescence imaging. Mice treated with the anti-α5β1 antibody h18C12.v6.1.5 in combination with anti-VEGF had a reduced tumor burden relative to mice treated with anti-VEGF alone. The results are shown in FIG. 13.

All publications (including, e.g., patents, published patent applications, and Genbank Accession Nos.) cited herein are hereby incorporated by reference in their entirety for all purposes as if each reference were specifically and individually incorporated by reference.

We claim:

1. An isolated nucleic acid molecule encoding an anti-α5β1 antibody comprising
   a VL domain comprising a CDR-L1 comprising TL-S/T-S/P/T-Q/N-H-F/S-T/I-Y-K/T-I-G/D/S (SEQ ID NO:15); a CDR-L2 comprising L/I-N/T-S-D/H/S-G/S-S/L/T-H/Y-N/K/Q/I-K/T-G/A-D/S/V (SEQ ID NO:16); a CDR-L3 comprising G/A-S/A/Y-S/Y-Y-S/A/Y-S/Y/T-GY-V/I (SEQ ID NO:17); and
   a VH domain comprising a CDR-H1 comprising GFTFS-N/A-RW-I/V-Y (SEQ ID NO:18); a CDR-H2 comprising GIKTKP-N/A/T-I/R-YAT-E/Q-YADSVKG (SEQ ID NO:19); and a CDR-H3 comprising L/V-TG-M/K-R/K-YFDY (SEQ ID NO:20).

2. A host cell comprising the nucleic acid of claim 1.

3. The isolated nucleic acid of claim 1, wherein the VL domain comprises a sequence set forth in any one of SEQ ID NOs: 3-8 and the VH domain comprises a sequence set forth in any one of SEQ ID NOs: 11-14.

4. The isolated nucleic acid of claim 1, wherein the VL domain comprises the sequence set forth in SEQ ID NOs: 8 and the VH domain comprises the sequence set forth in SEQ ID NO: 14.

5. An expression vector comprising the nucleic acid of claim 1.

6. The isolated nucleic acid molecule of claim 1, wherein the VL domain comprises a CDR-L1 comprising TLSSQH-STYTI of SEQ ID NO: 21; a CDR-L2 comprising LNS-DSSHNKGSGIPD (residues 50-60 of SEQ ID NO: 8); a CDR-L3 comprising AAYYAYGYV of SEQ ID NO: 30; and a VH domain comprises a CDR-H1 comprising GFTFSAR-WIY of SEQ ID NO:34; a CDR-H2 comprising GIKTK-PAIYATEYADSVKGRFT (residues 50-68 of SEQ ID NO:14); and a CDR-H3 comprising LTGMKYFDY of SEQ ID NO:39.

7. A method of making an anti-α5β1 antibody comprising culturing the host cell of claim 2 so that the antibody is produced and recovering the antibody.

8. A host cell comprising the nucleic acid of claim 6.

9. A method of making an anti-α5β1 antibody comprising culturing the host cell of claim 8 so that the antibody is produced and recovering the antibody.

* * * * *

```
                        SEQUENCE LISTING

<160> NUMBER OF SEQ ID NOS: 40

<210> SEQ ID NO 1
<211> LENGTH: 110
<212> TYPE: PRT
<213> ORGANISM: Homo sapien
<220> FEATURE:
<221> NAME/KEY: Variant
<222> LOCATION: 22-36
<223> OTHER INFORMATION: X is any amino acid
<220> FEATURE:
<221> NAME/KEY: Unsure
<222> LOCATION: 22-36,52-62,95-105
<223> OTHER INFORMATION: Unknown amino acid
<220> FEATURE:
<221> NAME/KEY: Variant
<222> LOCATION: 52-62
<223> OTHER INFORMATION: X is any amino acid
<220> FEATURE:
<221> NAME/KEY: Variant
<222> LOCATION: 95-105
<223> OTHER INFORMATION: X is any amino acid

<400> SEQUENCE: 1

Ser Glu Leu Thr Gln Asp Pro Ala Val Ser Val Ala Leu Gly Gln
  1               5                  10                  15

Thr Val Arg Ile Thr Cys Xaa Xaa Xaa Xaa Xaa Xaa Xaa Xaa Xaa
                 20                  25                  30

Xaa Xaa Xaa Xaa Xaa Xaa Trp Tyr Gln Gln Lys Pro Gly Gln Ala
                 35                  40                  45

Pro Val Leu Val Ile Tyr Xaa Xaa Xaa Xaa Xaa Xaa Xaa Xaa Xaa
                 50                  55                  60

Xaa Xaa Gly Ile Pro Asp Arg Phe Ser Gly Ser Ser Ser Gly Asn
                 65                  70                  75

Thr Ala Ser Leu Thr Ile Thr Gly Ala Gln Ala Glu Asp Glu Ala
                 80                  85                  90

Asp Tyr Tyr Cys Xaa Xaa Xaa Xaa Xaa Xaa Xaa Xaa Xaa Xaa Xaa
                 95                 100                 105

Phe Gly Gly Gly Thr
                110

<210> SEQ ID NO 2
<211> LENGTH: 106
<212> TYPE: PRT
<213> ORGANISM: Cricetulus griseus

<400> SEQUENCE: 2

Gln Pro Val Leu Thr Gln Ser Pro Ser Ala Ser Ala Ser Leu Gly
  1               5                  10                  15

Asn Ser Val Lys Ile Thr Cys Thr Leu Ser Ser Gln His Ser Thr
                 20                  25                  30

Tyr Thr Ile Gly Trp Tyr Gln Gln His Pro Asp Lys Ala Pro Lys
                 35                  40                  45

Tyr Val Met Tyr Leu Asn Ser Asp Gly Ser His Asn Lys Gly Asp
```

```
                    50                  55                  60
Gly Ile Pro Asp Arg Phe Ser Gly Ser Ser Gly Ala His Arg
                65                  70                  75
Tyr Leu Ser Ile Ser Asn Ile Gln Pro Glu Asp Glu Ala Asp Tyr
            80                  85                  90
Phe Cys Gly Ser Ser Tyr Ser Ser Gly Tyr Val Phe Gly Ser Gly
                95                  100                 105
Thr

<210> SEQ ID NO 3
<211> LENGTH: 106
<212> TYPE: PRT
<213> ORGANISM: Homo sapien

<400> SEQUENCE: 3

Asp Ile Val Leu Thr Gln Ser Pro Ser Ala Ser Ala Ser Leu Gly
 1               5                  10                  15
Asn Ser Val Lys Ile Thr Cys Thr Leu Ser Ser Gln His Ser Thr
                20                  25                  30
Tyr Thr Ile Gly Trp Tyr Gln Gln His Pro Asp Lys Ala Pro Lys
                35                  40                  45
Tyr Val Met Tyr Leu Asn Ser Asp Gly Ser His Asn Lys Gly Asp
                50                  55                  60
Gly Ile Pro Asp Arg Phe Ser Gly Ser Ser Gly Ala His Arg
                65                  70                  75
Tyr Leu Ser Ile Ser Asn Ile Gln Pro Glu Asp Glu Ala Asp Tyr
                80                  85                  90
Phe Cys Gly Ser Ser Tyr Ser Ser Gly Tyr Val Phe Gly Ser Gly
                95                  100                 105
Thr

<210> SEQ ID NO 4
<211> LENGTH: 106
<212> TYPE: PRT
<213> ORGANISM: Homo sapien

<400> SEQUENCE: 4

Glu Pro Val Leu Thr Gln Ser Pro Ser Ala Ser Ala Ser Leu Gly
 1               5                  10                  15
Ala Ser Val Lys Leu Thr Cys Thr Leu Ser Ser Gln His Ser Thr
                20                  25                  30
Tyr Thr Ile Gly Trp Tyr Gln Gln Gln Pro Gly Lys Ala Pro Arg
                35                  40                  45
Tyr Leu Met Tyr Leu Asn Ser Asp Gly Ser His Asn Lys Gly Asp
                50                  55                  60
Gly Ile Pro Asp Arg Phe Ser Gly Ser Ser Gly Ala Asp Arg
                65                  70                  75
Tyr Leu Thr Ile Ser Asn Leu Gln Ser Glu Asp Glu Ala Asp Tyr
                80                  85                  90
Tyr Cys Gly Ser Ser Tyr Ser Ser Gly Tyr Val Phe Gly Gly Gly
                95                  100                 105
Thr

<210> SEQ ID NO 5
<211> LENGTH: 106
<212> TYPE: PRT
```

<213> ORGANISM: Homo sapien

<400> SEQUENCE: 5

Glu Pro Val Leu Thr Gln Ser Pro Ser Ala Ser Ala Ser Leu Gly
1               5                   10                  15

Ala Ser Val Lys Leu Thr Cys Thr Leu Ser Ser Gln His Ser Thr
            20                  25                  30

Tyr Thr Ile Gly Trp Tyr Gln Gln Pro Gly Lys Ala Pro Arg
        35                  40                  45

Tyr Leu Met Tyr Leu Asn Ser Asp Gly Ser His Asn Lys Gly Asp
        50                  55                  60

Gly Ile Pro Asp Arg Phe Ser Gly Ser Ser Gly Ala Asp Arg
65                  70                  75

Tyr Leu Thr Ile Ser Asn Leu Gln Ser Glu Asp Glu Ala Asp Tyr
            80                  85                  90

Tyr Cys Ala Ala Tyr Tyr Ala Tyr Gly Tyr Val Phe Gly Gly Gly
            95                  100                 105

Thr

<210> SEQ ID NO 6
<211> LENGTH: 106
<212> TYPE: PRT
<213> ORGANISM: Homo sapien

<400> SEQUENCE: 6

Ser Ser Glu Leu Thr Gln Asp Pro Ala Val Ser Val Ala Leu Gly
1               5                   10                  15

Gln Thr Val Arg Ile Thr Cys Thr Leu Ser Ser Gln His Ser Thr
            20                  25                  30

Tyr Thr Ile Gly Trp Tyr Gln Gln Lys Pro Gly Gln Ala Pro Val
        35                  40                  45

Tyr Leu Met Tyr Leu Asn Ser Ser Gly Ser His Asn Lys Gly Ser
        50                  55                  60

Gly Ile Pro Asp Arg Phe Ser Gly Ser Ser Gly Ala Thr Arg
65                  70                  75

Ser Leu Thr Ile Thr Asn Ala Gln Ala Glu Asp Glu Ala Asp Tyr
            80                  85                  90

Tyr Cys Ala Ala Tyr Tyr Ala Tyr Gly Tyr Val Phe Gly Gly Gly
            95                  100                 105

Thr

<210> SEQ ID NO 7
<211> LENGTH: 106
<212> TYPE: PRT
<213> ORGANISM: Homo sapien

<400> SEQUENCE: 7

Ser Ser Glu Leu Thr Gln Asp Pro Ala Val Ser Val Ala Leu Gly
1               5                   10                  15

Gln Thr Val Arg Ile Thr Cys Thr Leu Ser Ser Gln His Ser Thr
            20                  25                  30

Tyr Thr Ile Gly Trp Tyr Gln Gln Lys Pro Gly Gln Ala Pro Val
        35                  40                  45

Leu Val Ile Tyr Leu Asn Ser Ser Gly Ser His Asn Lys Gly Ser
        50                  55                  60

Gly Ile Pro Asp Arg Phe Ser Gly Ser Ser Ser Gly Ala Thr Arg

```
                        65                  70                  75

Ser Leu Thr Ile Thr Asn Ala Gln Ala Glu Asp Glu Ala Asp Tyr
                80                  85                  90

Tyr Cys Ala Ala Tyr Tyr Ala Tyr Gly Tyr Val Phe Gly Gly Gly
                95                 100                 105

Thr

<210> SEQ ID NO 8
<211> LENGTH: 106
<212> TYPE: PRT
<213> ORGANISM: Homo sapien

<400> SEQUENCE: 8

Ser Ser Glu Leu Thr Gln Asp Pro Ala Val Ser Val Ala Leu Gly
 1               5                  10                  15

Gln Thr Val Arg Ile Thr Cys Thr Leu Ser Ser Gln His Ser Thr
                20                  25                  30

Tyr Thr Ile Gly Trp Tyr Gln Gln Lys Pro Gly Gln Ala Pro Val
                35                  40                  45

Tyr Leu Met Tyr Leu Asn Ser Asp Ser Ser His Asn Lys Gly Ser
                50                  55                  60

Gly Ile Pro Asp Arg Phe Ser Gly Ser Ser Ser Gly Ala Thr Arg
                65                  70                  75

Ser Leu Thr Ile Thr Asn Ala Gln Ala Glu Asp Glu Ala Asp Tyr
                80                  85                  90

Tyr Cys Ala Ala Tyr Tyr Ala Tyr Gly Tyr Val Phe Gly Gly Gly
                95                 100                 105

Thr

<210> SEQ ID NO 9
<211> LENGTH: 114
<212> TYPE: PRT
<213> ORGANISM: Cricetulus griseus

<400> SEQUENCE: 9

Glu Val His Leu Val Glu Ser Gly Gly Asp Leu Val Gln Pro Gly
 1               5                  10                  15

Ser Ser Leu Lys Leu Ser Cys Ala Ala Ser Gly Phe Thr Phe Ser
                20                  25                  30

Asn Arg Trp Ile Tyr Trp Val Arg Gln Ala Pro Gly Lys Gly Leu
                35                  40                  45

Glu Trp Val Gly Gly Ile Lys Thr Lys Pro Asn Ile Tyr Ala Thr
                50                  55                  60

Glu Tyr Ala Asp Ser Val Lys Gly Arg Phe Thr Ile Ser Arg Asp
                65                  70                  75

Asp Ser Lys Asn Ser Leu Tyr Leu Gln Met Asn Thr Leu Arg Val
                80                  85                  90

Asp Asp Thr Ala Ile Tyr Tyr Cys Thr Ser Leu Thr Gly Met Arg
                95                 100                 105

Tyr Phe Asp Tyr Trp Gly Gln Gly Thr
                110

<210> SEQ ID NO 10
<211> LENGTH: 116
<212> TYPE: PRT
<213> ORGANISM: Homo sapien
<220> FEATURE:
```

<221> NAME/KEY: Variant
<222> LOCATION: 26-35
<223> OTHER INFORMATION: X is any amino acid
<220> FEATURE:
<221> NAME/KEY: Unsure
<222> LOCATION: 26-35,52-70,103-111
<223> OTHER INFORMATION: Unknown amino acid
<220> FEATURE:
<221> NAME/KEY: Variant
<222> LOCATION: 52-70
<223> OTHER INFORMATION: X is any amino acid
<220> FEATURE:
<221> NAME/KEY: Variant
<222> LOCATION: 103-111
<223> OTHER INFORMATION: X is any amino acid

<400> SEQUENCE: 10

| Glu | Val | Gln | Leu | Val | Glu | Ser | Gly | Gly | Gly | Leu | Val | Gln | Pro | Gly |
|---|---|---|---|---|---|---|---|---|---|---|---|---|---|---|
| 1 | | | | 5 | | | | | 10 | | | | | 15 |

Gly Ser Leu Arg Leu Ser Cys Ala Ala Ser Xaa Xaa Xaa Xaa Xaa
                20                  25                  30

Xaa Xaa Xaa Xaa Xaa Trp Asn Trp Val Arg Gln Ala Pro Gly Lys
                35                  40                  45

Gly Leu Glu Trp Val Ser Xaa Xaa Xaa Xaa Xaa Xaa Xaa Xaa Xaa
                50                  55                  60

Xaa Xaa Xaa Xaa Xaa Xaa Xaa Xaa Xaa Xaa Arg Phe Thr Ile Ser
                65                  70                  75

Arg Asp Asn Ser Lys Asn Thr Leu Tyr Leu Gln Met Asn Ser Leu
                80                  85                  90

Arg Ala Glu Asp Thr Ala Val Tyr Tyr Cys Ala Arg Xaa Xaa Xaa
                95                  100                 105

Xaa Xaa Xaa Xaa Xaa Xaa Trp Gly Gln Gly Thr
                110                 115

<210> SEQ ID NO 11
<211> LENGTH: 114
<212> TYPE: PRT
<213> ORGANISM: Homo sapien

<400> SEQUENCE: 11

Glu Val Gln Leu Val Glu Ser Gly Gly Gly Leu Val Gln Pro Gly
 1               5                   10                  15

Gly Ser Leu Arg Leu Ser Cys Ala Ala Ser Gly Phe Thr Phe Ser
                20                  25                  30

Asn Arg Trp Ile Tyr Trp Val Arg Gln Ala Pro Gly Lys Gly Leu
                35                  40                  45

Glu Trp Val Gly Gly Ile Lys Thr Lys Pro Asn Ile Tyr Ala Thr
                50                  55                  60

Glu Tyr Ala Asp Ser Val Lys Gly Arg Phe Thr Ile Ser Arg Asp
                65                  70                  75

Asp Ser Lys Asn Thr Leu Tyr Leu Gln Met Asn Ser Leu Arg Ala
                80                  85                  90

Glu Asp Thr Ala Val Tyr Tyr Cys Ala Arg Leu Thr Gly Met Arg
                95                  100                 105

Tyr Phe Asp Tyr Trp Gly Gln Gly Thr
                110

<210> SEQ ID NO 12
<211> LENGTH: 114
<212> TYPE: PRT
<213> ORGANISM: Homo sapien

<400> SEQUENCE: 12

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Asn Arg Trp Ile Tyr Trp Val Arg Gln Ala Pro Gly Lys Gly Leu
            35                  40                  45

Glu Trp Val Gly Gly Ile Lys Thr Lys Pro Asn Ile Tyr Ala Thr
            50                  55                  60

Glu Tyr Ala Asp Ser Val Lys Gly Arg Phe Thr Ile Ser Arg Asp
65                  70                  75

Asp Ser Lys Asn Thr Leu Tyr Leu Gln Met Asn Ser Leu Arg Ala
            80                  85                  90

Glu Asp Thr Ala Val Tyr Tyr Cys Ala Arg Leu Thr Gly Met Lys
            95                  100                 105

Tyr Phe Asp Tyr Trp Gly Gln Gly Thr
            110

<210> SEQ ID NO 13
<211> LENGTH: 114
<212> TYPE: PRT
<213> ORGANISM: Homo sapien

<400> SEQUENCE: 13

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Ala Arg Trp Ile Tyr Trp Val Arg Gln Ala Pro Gly Lys Gly Leu
            35                  40                  45

Glu Trp Val Gly Gly Ile Lys Thr Lys Pro Ala Ile Tyr Ala Thr
            50                  55                  60

Glu Tyr Ala Asp Ser Val Lys Gly Arg Phe Thr Ile Ser Arg Asp
65                  70                  75

Asp Ser Lys Asn Thr Leu Tyr Leu Gln Met Asn Ser Leu Arg Ala
            80                  85                  90

Glu Asp Thr Ala Val Tyr Tyr Cys Ala Arg Leu Thr Gly Met Lys
            95                  100                 105

Tyr Phe Asp Tyr Trp Gly Gln Gly Thr
            110

<210> SEQ ID NO 14
<211> LENGTH: 114
<212> TYPE: PRT
<213> ORGANISM: Homo sapien

<400> SEQUENCE: 14

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Ala Arg Trp Ile Tyr Trp Val Arg Gln Ala Pro Gly Lys Gly Leu
            35                  40                  45

Glu Trp Val Gly Gly Ile Lys Thr Lys Pro Ala Ile Tyr Ala Thr
            50                  55                  60

```
Glu Tyr Ala Asp Ser Val Lys Gly Arg Phe Thr Ile Ser Arg Asp
             65                  70                  75

Asp Ser Lys Asn Thr Leu Tyr Leu Gln Met Asn Ser Leu Arg Ala
         80                  85                  90

Glu Asp Thr Ala Val Tyr Tyr Cys Ala Arg Leu Thr Gly Met Lys
     95                 100                 105

Tyr Phe Asp Tyr Trp Gly Gln Gly Thr
            110

<210> SEQ ID NO 15
<211> LENGTH: 12
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 3
<223> OTHER INFORMATION: X is S or T
<220> FEATURE:
<221> NAME/KEY: Variant
<222> LOCATION: 4
<223> OTHER INFORMATION: X is S, P, or T
<220> FEATURE:
<221> NAME/KEY: Variant
<222> LOCATION: 5
<223> OTHER INFORMATION: X is Q or N
<220> FEATURE:
<221> NAME/KEY: Variant
<222> LOCATION: 7
<223> OTHER INFORMATION: X is F or S
<220> FEATURE:
<221> NAME/KEY: Variant
<222> LOCATION: 8
<223> OTHER INFORMATION: X is T or I
<220> FEATURE:
<221> NAME/KEY: Variant
<222> LOCATION: 10
<223> OTHER INFORMATION: X is K or T
<220> FEATURE:
<221> NAME/KEY: Variant
<222> LOCATION: 12
<223> OTHER INFORMATION: X is G, D, or S

<400> SEQUENCE: 15

Thr Leu Xaa Xaa Xaa His Xaa Xaa Tyr Xaa Ile Xaa
                 5                  10

<210> SEQ ID NO 16
<211> LENGTH: 11
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 1
<223> OTHER INFORMATION: X is L or I
<220> FEATURE:
<221> NAME/KEY: Variant
<222> LOCATION: 2
<223> OTHER INFORMATION: X is N or T
<220> FEATURE:
<221> NAME/KEY: Variant
<222> LOCATION: 4
<223> OTHER INFORMATION: X is D, H, or S
<220> FEATURE:
<221> NAME/KEY: Variant
<222> LOCATION: 5
<223> OTHER INFORMATION: X is G or S
<220> FEATURE:
<221> NAME/KEY: Variant
<222> LOCATION: 6
```

```
<223> OTHER INFORMATION: X is S, L, or T
<220> FEATURE:
<221> NAME/KEY: Variant
<222> LOCATION: 7
<223> OTHER INFORMATION: X is H or Y
<220> FEATURE:
<221> NAME/KEY: Variant
<222> LOCATION: 8
<223> OTHER INFORMATION: X is N, K, Q or I
<220> FEATURE:
<221> NAME/KEY: Variant
<222> LOCATION: 9
<223> OTHER INFORMATION: X is K or T
<220> FEATURE:
<221> NAME/KEY: Variant
<222> LOCATION: 10
<223> OTHER INFORMATION: X is G or A
<220> FEATURE:
<221> NAME/KEY: Variant
<222> LOCATION: 11
<223> OTHER INFORMATION: X is D, S, or V

<400> SEQUENCE: 16

Xaa Xaa Ser Xaa Xaa Xaa Xaa Xaa Xaa Xaa Xaa
                 5                   10

<210> SEQ ID NO 17
<211> LENGTH: 9
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 1
<223> OTHER INFORMATION: X is G or A
<220> FEATURE:
<221> NAME/KEY: Variant
<222> LOCATION: 2
<223> OTHER INFORMATION: X is S, A, or Y
<220> FEATURE:
<221> NAME/KEY: Variant
<222> LOCATION: 3
<223> OTHER INFORMATION: X is S or Y
<220> FEATURE:
<221> NAME/KEY: Variant
<222> LOCATION: 5
<223> OTHER INFORMATION: X is S, A, or Y
<220> FEATURE:
<221> NAME/KEY: Variant
<222> LOCATION: 6
<223> OTHER INFORMATION: X is S, Y, or T
<220> FEATURE:
<221> NAME/KEY: Variant
<222> LOCATION: 9
<223> OTHER INFORMATION: X is V or I

<400> SEQUENCE: 17

Xaa Xaa Xaa Tyr Xaa Xaa Gly Tyr Xaa
                 5

<210> SEQ ID NO 18
<211> LENGTH: 10
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 6
<223> OTHER INFORMATION: X is N or A
<220> FEATURE:
<221> NAME/KEY: Variant
<222> LOCATION: 9
<223> OTHER INFORMATION: X is I or V
```

```
<400> SEQUENCE: 18

Gly Phe Thr Phe Ser Xaa Arg Trp Xaa Tyr
                5                   10

<210> SEQ ID NO 19
<211> LENGTH: 19
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 7
<223> OTHER INFORMATION: X is N, A, or T
<220> FEATURE:
<221> NAME/KEY: Variant
<222> LOCATION: 8
<223> OTHER INFORMATION: X is I or R
<220> FEATURE:
<221> NAME/KEY: Variant
<222> LOCATION: 12
<223> OTHER INFORMATION: X is E or Q

<400> SEQUENCE: 19

Gly Ile Lys Thr Lys Pro Xaa Xaa Tyr Ala Thr Xaa Tyr Ala Asp
 1               5                  10                  15

Ser Val Lys Gly

<210> SEQ ID NO 20
<211> LENGTH: 9
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: 1
<223> OTHER INFORMATION: X is L or V
<220> FEATURE:
<221> NAME/KEY: Variant
<222> LOCATION: 4
<223> OTHER INFORMATION: X is M or K
<220> FEATURE:
<221> NAME/KEY: Variant
<222> LOCATION: 5
<223> OTHER INFORMATION: X is R or K

<400> SEQUENCE: 20

Xaa Thr Gly Xaa Xaa Tyr Phe Asp Tyr
                 5

<210> SEQ ID NO 21
<211> LENGTH: 12
<212> TYPE: PRT
<213> ORGANISM: Artificial sequence
<220> FEATURE:
<223> OTHER INFORMATION: sequence is synthesized

<400> SEQUENCE: 21

Thr Leu Ser Ser Gln His Ser Thr Tyr Thr Ile Gly
                 5                  10

<210> SEQ ID NO 22
<211> LENGTH: 12
<212> TYPE: PRT
<213> ORGANISM: Artificial sequence
<220> FEATURE:
<223> OTHER INFORMATION: sequence is synthesized
```

```
<400> SEQUENCE: 22

Thr Leu Ser Pro Gln His Phe Thr Tyr Lys Ile Asp
                5                   10

<210> SEQ ID NO 23
<211> LENGTH: 12
<212> TYPE: PRT
<213> ORGANISM: Artificial sequence
<220> FEATURE:
<223> OTHER INFORMATION: sequence is synthesized

<400> SEQUENCE: 23

Thr Leu Ser Ser Asn His Ser Ile Tyr Thr Ile Ser
                5                   10

<210> SEQ ID NO 24
<211> LENGTH: 12
<212> TYPE: PRT
<213> ORGANISM: Artificial sequence
<220> FEATURE:
<223> OTHER INFORMATION: sequence is synthesized

<400> SEQUENCE: 24

Thr Leu Thr Thr Gln His Ser Thr Tyr Thr Ile Gly
                5                   10

<210> SEQ ID NO 25
<211> LENGTH: 11
<212> TYPE: PRT
<213> ORGANISM: Artificial sequence
<220> FEATURE:
<223> OTHER INFORMATION: sequence is synthesized

<400> SEQUENCE: 25

Leu Asn Ser Asp Gly Ser His Asn Lys Gly Asp
                5                   10

<210> SEQ ID NO 26
<211> LENGTH: 11
<212> TYPE: PRT
<213> ORGANISM: Artificial sequence
<220> FEATURE:
<223> OTHER INFORMATION: sequence is synthesized

<400> SEQUENCE: 26

Ile Asn Ser Asp Gly Ser His Lys Lys Gly Val
                5                   10

<210> SEQ ID NO 27
<211> LENGTH: 11
<212> TYPE: PRT
<213> ORGANISM: Artificial sequence
<220> FEATURE:
<223> OTHER INFORMATION: sequence is synthesized

<400> SEQUENCE: 27

Leu Thr Ser His Gly Leu His Gln Lys Gly Val
                5                   10

<210> SEQ ID NO 28
<211> LENGTH: 11
<212> TYPE: PRT
<213> ORGANISM: Artificial sequence
<220> FEATURE:
<223> OTHER INFORMATION: sequence is synthesized

<400> SEQUENCE: 28
```

-continued

Leu Asn Ser Asp Ser Thr Tyr Ile Thr Ala Val
                5                   10

<210> SEQ ID NO 29
<211> LENGTH: 9
<212> TYPE: PRT
<213> ORGANISM: Artificial sequence
<220> FEATURE:
<223> OTHER INFORMATION: sequence is synthesized

<400> SEQUENCE: 29

Gly Ser Ser Tyr Ser Ser Gly Tyr Val
                5

<210> SEQ ID NO 30
<211> LENGTH: 9
<212> TYPE: PRT
<213> ORGANISM: Artificial sequence
<220> FEATURE:
<223> OTHER INFORMATION: sequence is synthesized

<400> SEQUENCE: 30

Ala Ala Tyr Tyr Ala Tyr Gly Tyr Val
                5

<210> SEQ ID NO 31
<211> LENGTH: 9
<212> TYPE: PRT
<213> ORGANISM: Artificial sequence
<220> FEATURE:
<223> OTHER INFORMATION: sequence is synthesized

<400> SEQUENCE: 31

Gly Tyr Ser Tyr Tyr Ser Gly Tyr Val
                5

<210> SEQ ID NO 32
<211> LENGTH: 9
<212> TYPE: PRT
<213> ORGANISM: Artificial sequence
<220> FEATURE:
<223> OTHER INFORMATION: sequence is synthesized

<400> SEQUENCE: 32

Gly Ser Ser Tyr Ser Thr Gly Tyr Val
                5

<210> SEQ ID NO 33
<211> LENGTH: 9
<212> TYPE: PRT
<213> ORGANISM: Artificial sequence
<220> FEATURE:
<223> OTHER INFORMATION: sequence is synthesized

<400> SEQUENCE: 33

Gly Ala Ser Tyr Ser Ser Gly Tyr Ile
                5

<210> SEQ ID NO 34
<211> LENGTH: 10
<212> TYPE: PRT
<213> ORGANISM: Artificial sequence
<220> FEATURE:
<223> OTHER INFORMATION: sequence is synthesized

<400> SEQUENCE: 34

Gly Phe Thr Phe Ser Asn Arg Trp Ile Tyr
              5               10

<210> SEQ ID NO 35
<211> LENGTH: 10
<212> TYPE: PRT
<213> ORGANISM: Artificial sequence
<220> FEATURE:
<223> OTHER INFORMATION: sequence is synthesized

<400> SEQUENCE: 35

Gly Phe Thr Phe Ser Asn Arg Trp Val Tyr
              5               10

<210> SEQ ID NO 36
<211> LENGTH: 19
<212> TYPE: PRT
<213> ORGANISM: Artificial sequence
<220> FEATURE:
<223> OTHER INFORMATION: sequence is synthesized

<400> SEQUENCE: 36

Gly Ile Lys Thr Lys Pro Asn Ile Tyr Ala Thr Glu Tyr Ala Asp
1          5           10          15

Ser Val Lys Gly

<210> SEQ ID NO 37
<211> LENGTH: 19
<212> TYPE: PRT
<213> ORGANISM: Artificial sequence
<220> FEATURE:
<223> OTHER INFORMATION: sequence is synthesized

<400> SEQUENCE: 37

Gly Ile Lys Thr Lys Pro Thr Arg Tyr Ala Thr Gln Tyr Ala Asp
1          5           10          15

Ser Val Lys Gly

<210> SEQ ID NO 38
<211> LENGTH: 9
<212> TYPE: PRT
<213> ORGANISM: Artificial sequence
<220> FEATURE:
<223> OTHER INFORMATION: sequence is synthesized

<400> SEQUENCE: 38

Leu Thr Gly Met Arg Tyr Phe Asp Tyr
              5

<210> SEQ ID NO 39
<211> LENGTH: 9
<212> TYPE: PRT
<213> ORGANISM: Artificial sequence
<220> FEATURE:
<223> OTHER INFORMATION: sequence is synthesized

<400> SEQUENCE: 39

Leu Thr Gly Met Lys Tyr Phe Asp Tyr
              5

<210> SEQ ID NO 40
<211> LENGTH: 9
<212> TYPE: PRT
<213> ORGANISM: Artificial sequence
<220> FEATURE:
<223> OTHER INFORMATION: sequence is synthesized -continued

<400> SEQUENCE: 40

Val Thr Gly Met Arg Tyr Phe Asp Tyr
                5